United States Patent [19]

Tanaka et al.

[11] Patent Number: 5,237,404
[45] Date of Patent: Aug. 17, 1993

[54] INSPECTION APPARATUS WITH IMPROVED DETECTION OF SURFACE DEFECTS OVER LARGE AND CURVED SURFACES

[75] Inventors: Kazumoto Tanaka, Hiroshima; Hidenori Ishiide, Higashihiroahima; Tsuyoshi Sugihara, Hiroshima; Akinori Utsunomiya, Hiroshima; Tatsumi Makimae, Higashihiroshima, all of Japan

[73] Assignee: Mazda Motor Corporation, Hiroshima, Japan

[21] Appl. No.: 723,174

[22] Filed: Jun. 28, 1991

[30] Foreign Application Priority Data

| Jun. 28, 1990 | [JP] | Japan | 2-172457 |
| Aug. 28, 1990 | [JP] | Japan | 2-227498 |
| Aug. 28, 1990 | [JP] | Japan | 2-227499 |
| Nov. 30, 1990 | [JP] | Japan | 2-339569 |
| Jun. 5, 1991 | [JP] | Japan | 3-134092 |
| Jun. 5, 1991 | [JP] | Japan | 3-134093 |

[51] Int. Cl.$^5$ ............................................. H04N 7/18
[52] U.S. Cl. ............................................ 358/106; 358/101; 356/376
[58] Field of Search .................. 358/106, 101, 107; 356/387, 349, 237, 372, 376; 250/572; 901/46, 47

[56] References Cited

U.S. PATENT DOCUMENTS

| 4,559,451 | 12/1985 | Carl | 250/572 X |
| 4,629,319 | 12/1986 | Clarke et al. | |
| 4,742,237 | 5/1988 | Ozawa | |
| 4,868,404 | 9/1989 | Hajime | |
| 5,064,291 | 11/1991 | Reiser | 356/372 |
| 5,072,128 | 12/1991 | Hayano et al. | 356/237 X |
| 5,119,434 | 6/1992 | Bishop et al. | 358/106 X |
| 5,129,009 | 7/1992 | Lebeau | 358/106 |

FOREIGN PATENT DOCUMENTS

| 2439988 | 3/1976 | Fed. Rep. of Germany . |
| 3813662A1 | 11/1988 | Fed. Rep. of Germany . |
| 62-233710 | 10/1987 | Japan . |

OTHER PUBLICATIONS

PCT Publication No. WO 89/01146 dated Feb. 9, 1989.
Official Office Action date May 20, 1992 issued in the matter of P 4121 464.1-52-Mazda Motor Corporation (with English Translation).

*Primary Examiner*—Victor R. Kostak

[57] ABSTRACT

A surface defect inspection apparatus includes a light radiation source, arranged to oppose a surface to be inspected serving as a mirror surface, for radiating light having a predetermined change pattern toward the surface to be inspected, a camera mechanism for receiving an image of the light radiation source, reflected by the surface to be inspected and forming a received-light image corresponding to the change pattern of the light radiation source, and a discriminator for discriminating a surface defect portion on the surface to be inspected by discriminating a portion whose change pattern is different from the change pattern on the basis of the received-light image formed by the camera mechanism.

21 Claims, 21 Drawing Sheets

$X_2$ $X_2$

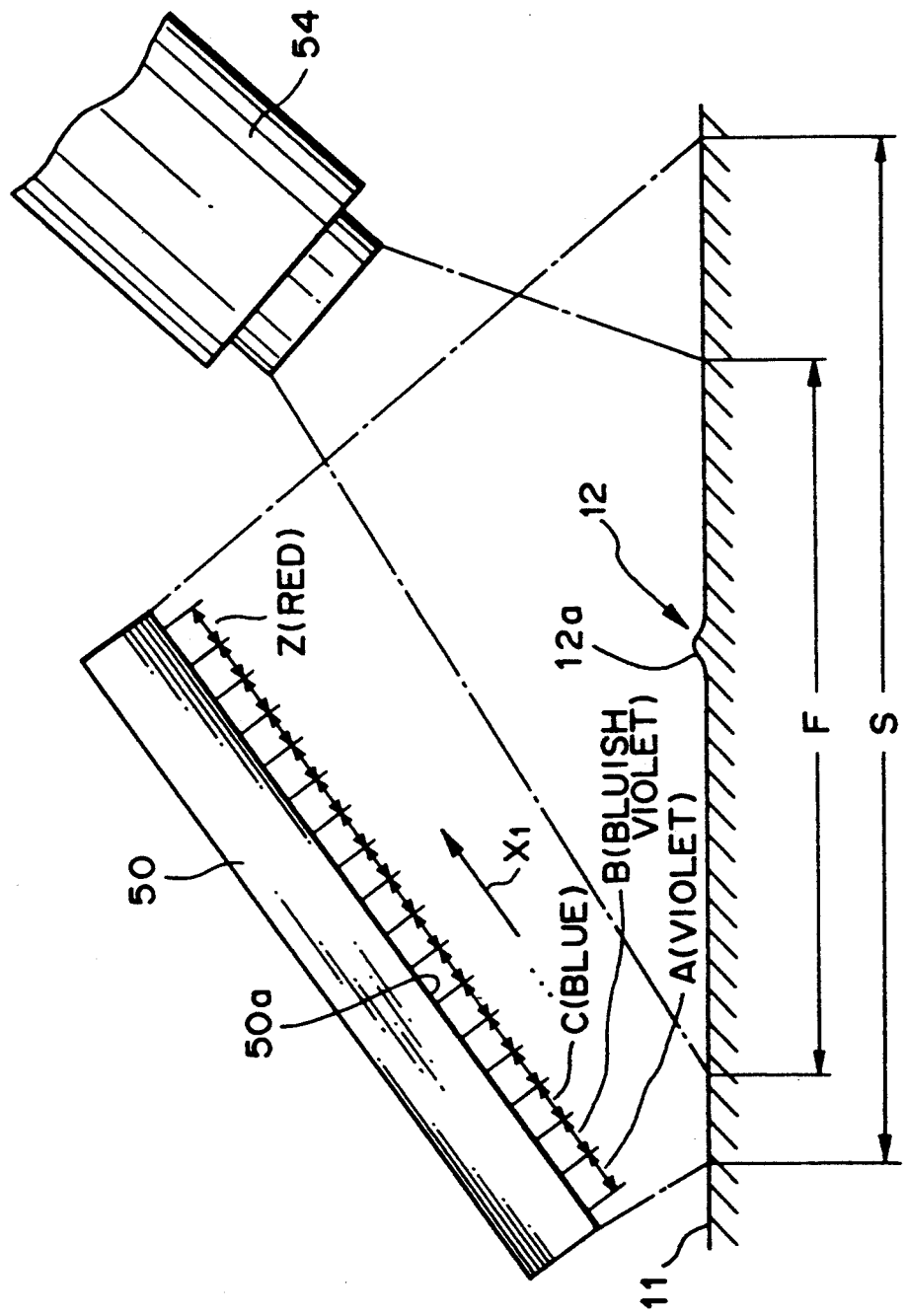

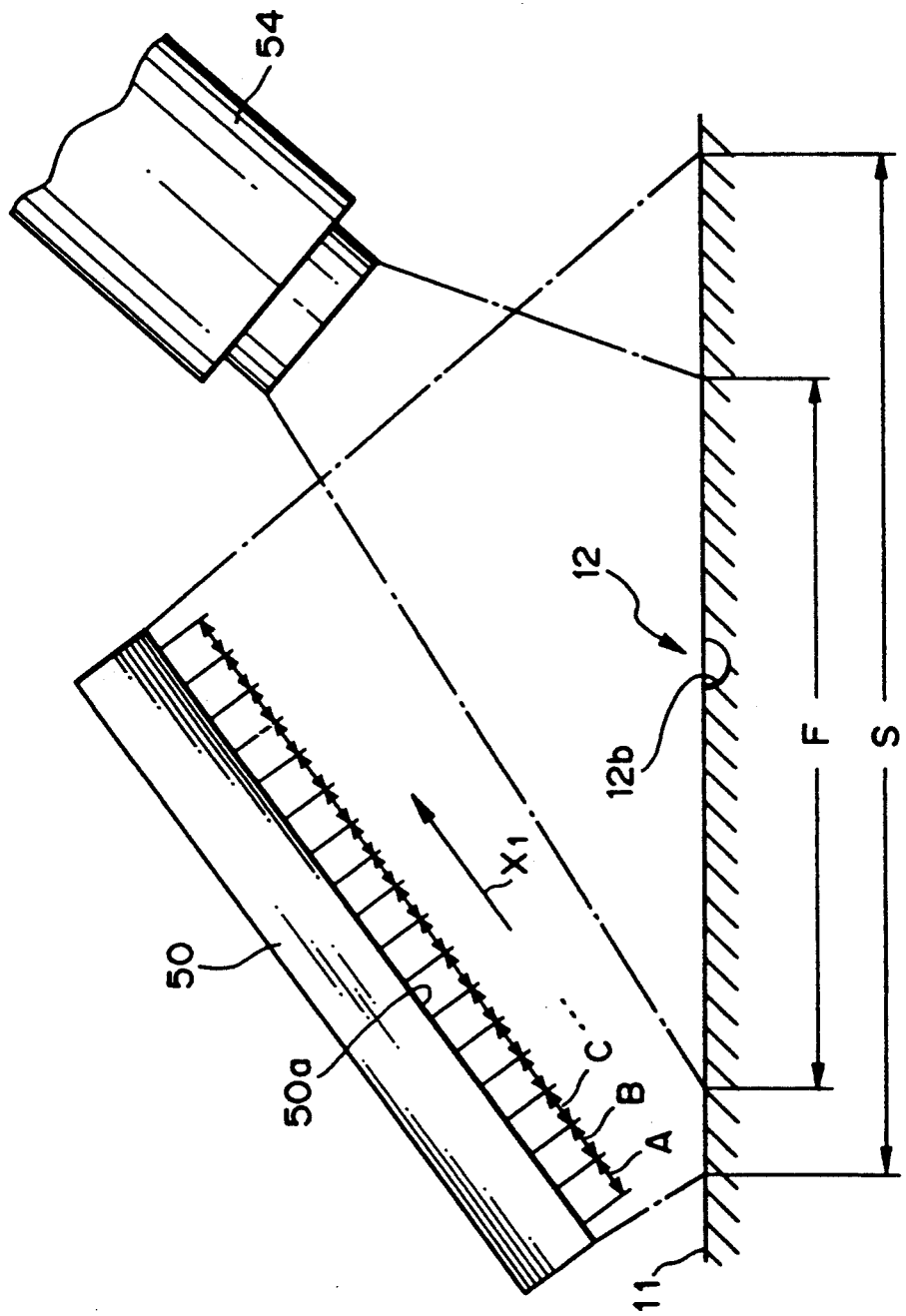

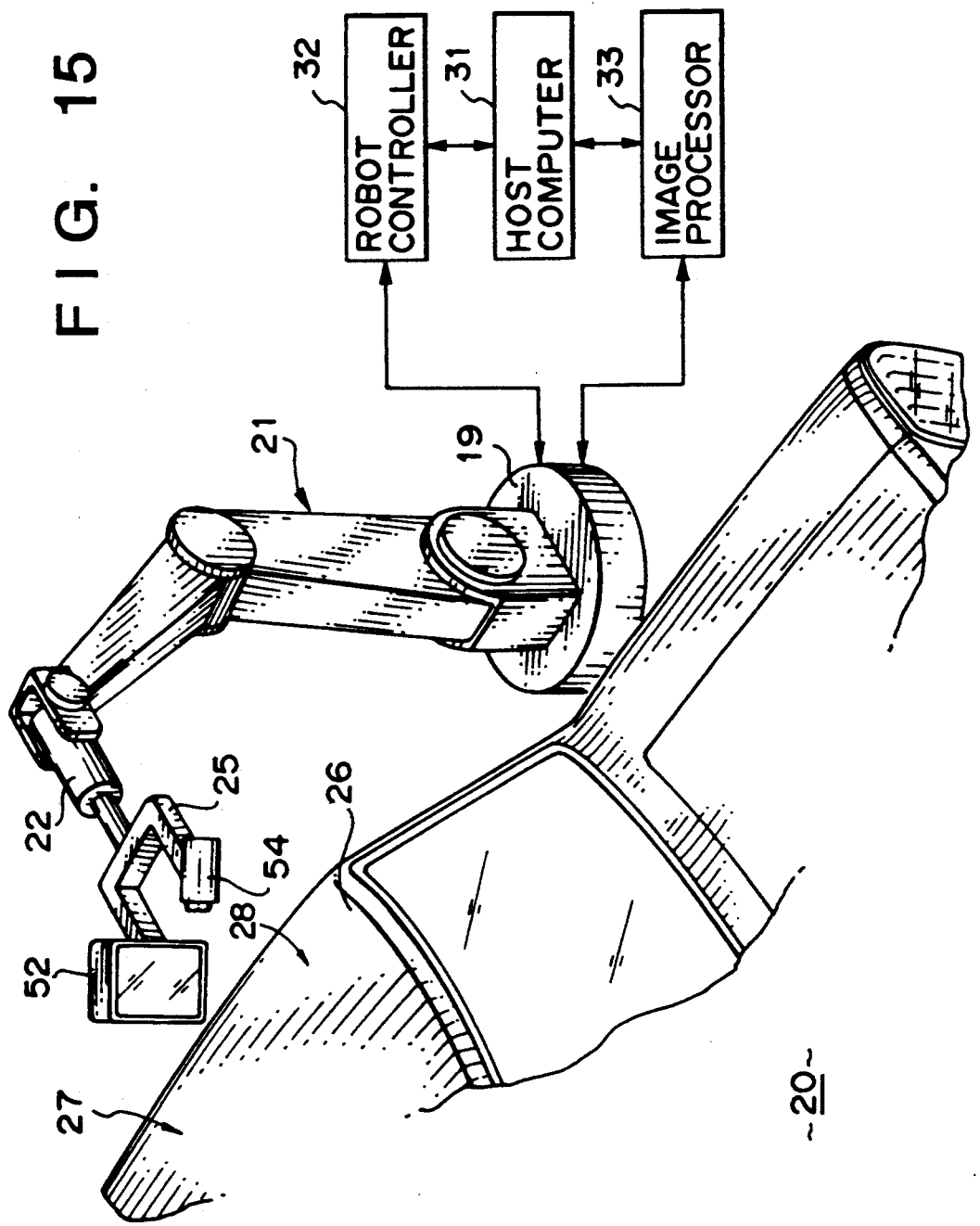

INSPECTION APPARATUS WITH IMPROVED DETECTION OF SURFACE DEFECTS OVER LARGE AND CURVED SURFACES

BACKGROUND OF THE INVENTION

The present invention relates to a surface defect inspection apparatus for radiating light on a surface to be inspected, and detecting the presence/absence of a surface defect such as a painting defect from light reflected by the surface.

In a manufacturing line of a vehicle such as an automobile, a vehicle body is normally painted in a painting station arranged in the manufacturing line. After the vehicle body is painted in the painting station, a painting defect caused by the painting process is inspected. The painting defect is conventionally inspected by a visual inspection of a person. In the visual inspection, a small defect portion must be found from a painted surface. For this reason, the visual inspection exerts a mentally and physically heavy load on an inspector.

As a technique for inspecting a painting defect not using a visual inspection of an inspector, for example, Japanese Patent Laid-Open No. 62-233710 discloses an inspection technique wherein light is radiated on a surface to be inspected of an object, light reflected by the surface is projected onto a screen, and a surface defect of the surface to be inspected is automatically detected on the basis of sharpness of the projected image.

Therefore, upon application of the technique disclosed in the above-mentioned prior art, a painting defect on a painted surface of a vehicle body can be automatically detected, and an inspector can be free from a conventional visual inspection operation.

When the surface inspection technique by means of light radiation disclosed in the above-mentioned prior art is applied to an automatic inspection of painting of a vehicle body, as shown in FIG. 1, the following inspection apparatus may be proposed. That is, this apparatus utilizes mirror-surface reflectance of a painted surface Y, and linear (or spot-like) light is radiated from a light source $A_1$ onto the painted surface Y, thereby forming a light radiation region sufficiently smaller than a camera field F of a CCD camera B to be described below. Light reflected by the light radiation region is received by the CCD camera B.

In this inspection apparatus, a received-light image C formed by the CCD camera B is as shown in FIG. 2, and the light radiation region of the painted surface Y is detected as a bright line D in the entirely dark received-light image C covering the camera field F. In this case, when a painting defect portion X assumed to have a spherical surface is present in the light radiation region, regular reflection occurs on the spherical surface of the painting defect portion X. More specifically, on the painting defect portion X, a surrounding background portion including the defect portion X is projected as a relatively wide range including the light source $A_1$ in a reduced scale. The image projected on the painting defect portion X includes the light source $A_1$ which is bright but is projected in a reduced scale, and a wide dark surrounding portion. Therefore, paying attention to an incident light amount of the painting defect portion X with respect to a camera light-receiving surface, the light amount is decreased in a portion corresponding to the dark surrounding portion around the light source A, and as a result, the surface defect portion X is projected in black in the bright line D.

In this manner, the black point is discriminated by the image processing technique, thereby allowing detection of the painting defect portion X. According to this inspection apparatus, since light is linearly radiated on the painted surface Y in a narrow range, even if a radiation light amount is small, a regular reflection direction of light incident on the light radiation region is changed by the painting defect portion X, and a clear light amount difference received by the camera B is formed between the painting defect portion X and the remaining portion. As a result, a small defect can be detected.

However, since light radiation is performed within a narrow range, the light radiation region is too small for the camera field F, while the defect portion X which can be detected by the camera B must be present inside or near the light radiation region (i.e., a line image in the received-light image). For this reason, a surface inspection using only a portion of the camera field F can only be performed, resulting in poor inspection efficiency.

When an object to be inspected is a painted surface of a vehicle body, the inspection is performed while moving the light source $A_1$ and the CCD camera B along the painted surface of the vehicle body by a robot apparatus. However, the vehicle body is constituted by many curved surfaces having different curvatures. For this reason, when an inspection portion is moved to these curved surface portions, a linear radiation pattern formed on the vehicle body surface by the light source $A_1$, and hence, the line image D in the received-light image C of the camera B is also distorted, as shown in FIG. 3. As a result, in the worst case, the line image D falls outside the camera field F. For this reason, a normal inspection is disturbed.

As for a vehicle body of a vehicle such as an automobile, it is difficult to perform a normal inspection of a painted surface, and the robot apparatus must undergo complicated control to allow the line image D to always fall within the camera field F.

In order to solve the above-mentioned problem, as shown in FIG. 4, the painted surface Y is irradiated with light from a light source $A_2$ having a wide light radiation region, so that light is two-dimensionally, i.e., widely radiated in a range equivalent to or larger than the camera field F. The wide light radiation region is detected by the camera B.

However, when the painted surface Y is irradiated with light over a wide range, a radiation light amount is considerably increased, and halation of light on the painting defect portion X occurs. As a result, the small painting defect portion X cannot be clearly detected. More specifically, an image projected on the painting defect portion X almost corresponds to only the light source $A_2$, and the painting defect portion X is also projected bright. Therefore, paying attention to an incident light amount of the painting defect portion X with respect to a camera light-receiving surface, a light amount on a portion irradiated with light from the light source $A_2$ becomes almost equal to a light amount on a portion projected on the painting defect portion X. As a result, the bright surface defect portion X is projected in the bright line D, and the CCD camera B cannot clearly detect the small painting defect portion X.

SUMMARY OF THE INVENTION

The present invention has been made in consideration of the above situation, and has as its object to provide a surface defect inspection apparatus which can precisely and efficiently detect the height and/or depth of a surface defect present on a surface to be inspected.

It is another object of the present invention to provide a surface inspection apparatus which can precisely and efficiently detect the position and three-dimensional pattern of a surface defect present on a surface to be inspected.

It is still another object of the present invention to provide a surface defect inspection apparatus which can precisely detect a small defect portion by image processing even when a surface to be inspected is irradiated with light over a wide range so as to inspect a surface detect on the surface to be inspected including a curved surface.

In order to achieve the above objects, according to a first aspect of the present invention, there is provided a surface defect inspection apparatus comprising light radiation means, arranged to oppose a surface to be inspected serving as a mirror surface, for radiating light having a predetermined change pattern toward the surface to be inspected, imaging means for imaging an image of the light radiation means reflected by the surface to be inspected and forming a received-light image corresponding to the change pattern of the light radiation means, and image processing means for detecting a surface defect portion on the surface to be inspected by discriminating a portion whose change pattern is largely different from the change pattern on the basis of the received-light image formed by the imaging means.

In the surface defect inspection apparatus according to a second aspect of the present invention, the light radiation means radiates light having a luminous intensity distribution including high-level and low-level portions toward the surface to be inspected.

In the surface defect inspection apparatus according to a third aspect of the present invention, the light radiation means radiates, toward the surface to be inspected, light having a luminous intensity distribution which is set so that a luminous intensity is gradually changed from high level to low level along a predetermined direction.

In the surface defect inspection apparatus according to a fourth aspect of the present invention, the light radiation means radiates light to have a luminous intensity distribution which is set such that high-level and low-level portions alternately appear.

In the surface defect inspection apparatus according to a fifth aspect of the present invention, the light radiation means radiates, toward the surface to be inspected, light having a wavelength distribution which is set such that a wavelength is gradually changed from a long wavelength to a short wavelength in a predetermined direction.

In the surface defect inspection apparatus according to a sixth aspect of the present invention, the light radiation means radiates, toward the surface to be inspected, light having a color pattern in which colors are sequentially changed in a predetermined order along a predetermined direction.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 13A and 13B are explanatory views for explaining the operation principle of a surface defect inspection apparatus according to a second embodiment of the present invention;

FIG. 15 is a perspective view showing the structure of the surface defect inspection apparatus according to the second embodiment of the present invention, which is applied to a painting defect inspection apparatus for a vehicle body;

DETAILED DESCRIPTION OF THE PREFERRED EMBODIMENTS

The structure of a surface defect inspection apparatus according to the first embodiment of the present invention will be described hereinafter.

Figure 1:
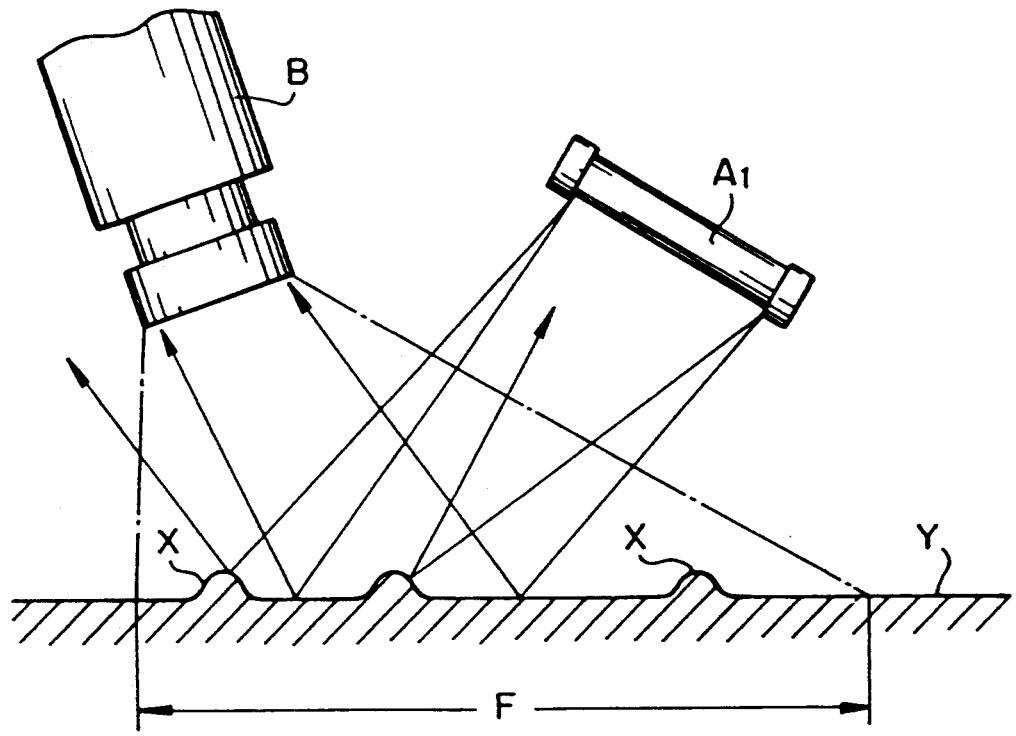
FIG. 1 is a schematic view showing an arrangement of a conventional surface defect inspection apparatus.
Figure 2:
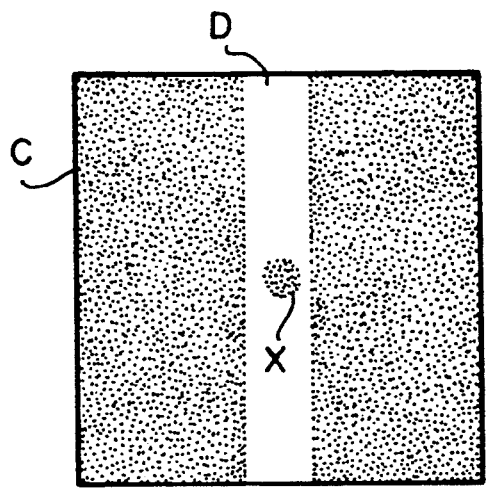
FIG. 2 is a view showing a formation state of an image obtained by a camera of the surface defect inspection apparatus shown in FIG. 1.
Figure 3:
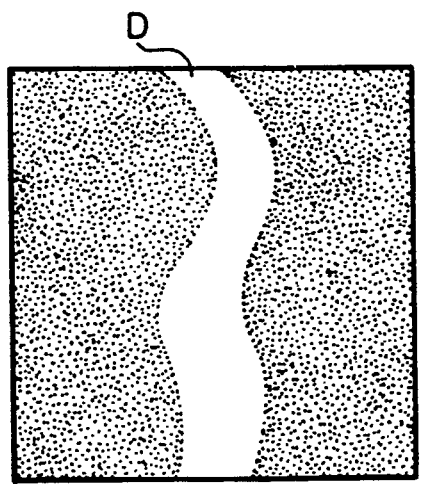
FIG. 3 is a view showing a formation state of an image obtained by a camera when a surface to be inspected is a curved surface.
Figure 4:
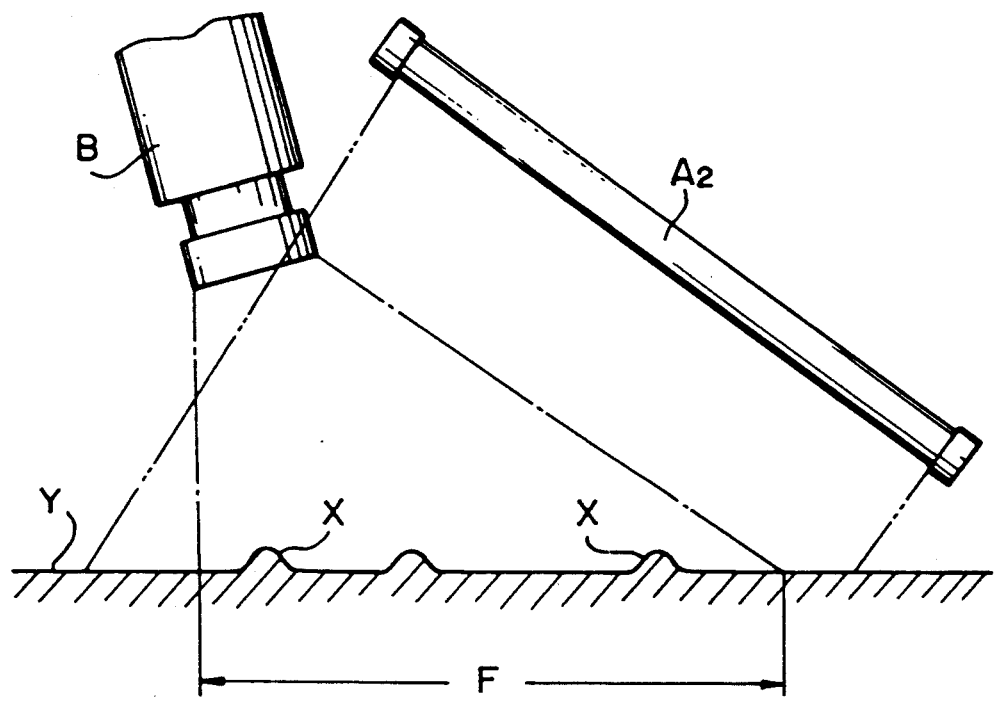
FIG. 4 is a schematic view showing an arrangement of another conventional surface defect inspection apparatus different from the conventional apparatus shown in FIG. 1.
Figure 5A:
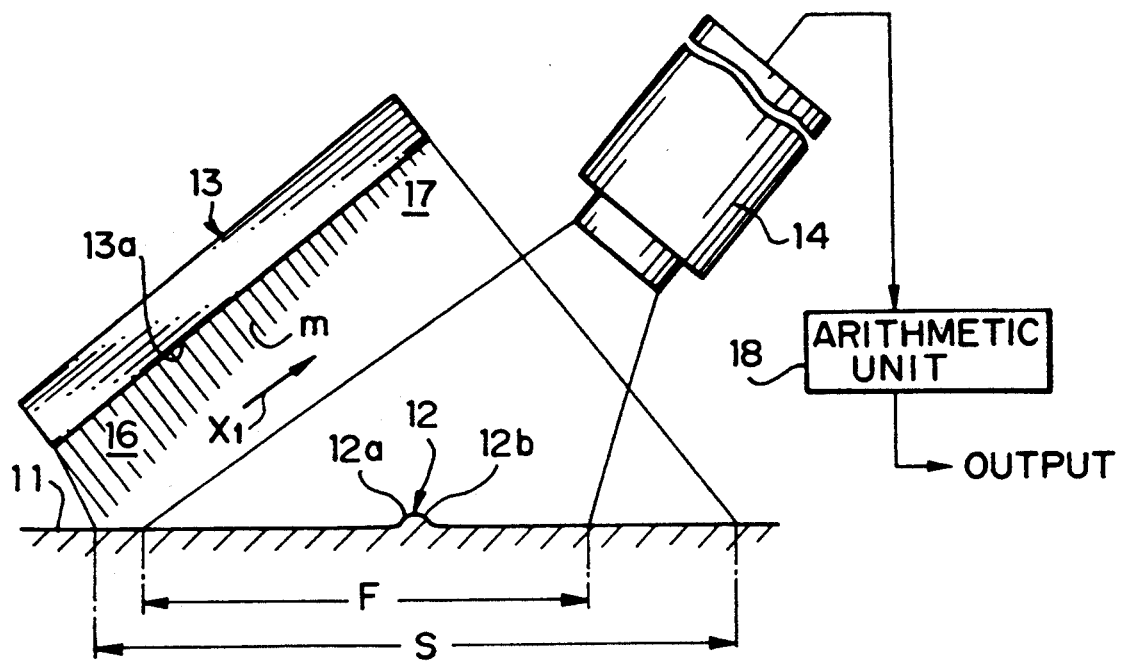
FIGS. 5A and 5B are explanatory views for explaining the operation principles of a surface defect inspection apparatus according to a first embodiment of the present invention.

The operation principle of the first embodiment will be described below with reference to FIGS. 5A to 10. FIG. 5A shows a case wherein a surface to be inspected (to be referred to as an inspection surface hereinafter) 11 has a convex defect portion 12, and FIG. 5B shows a case wherein the inspection surface 11 has a concave defect portion 12.

Figure 5B:
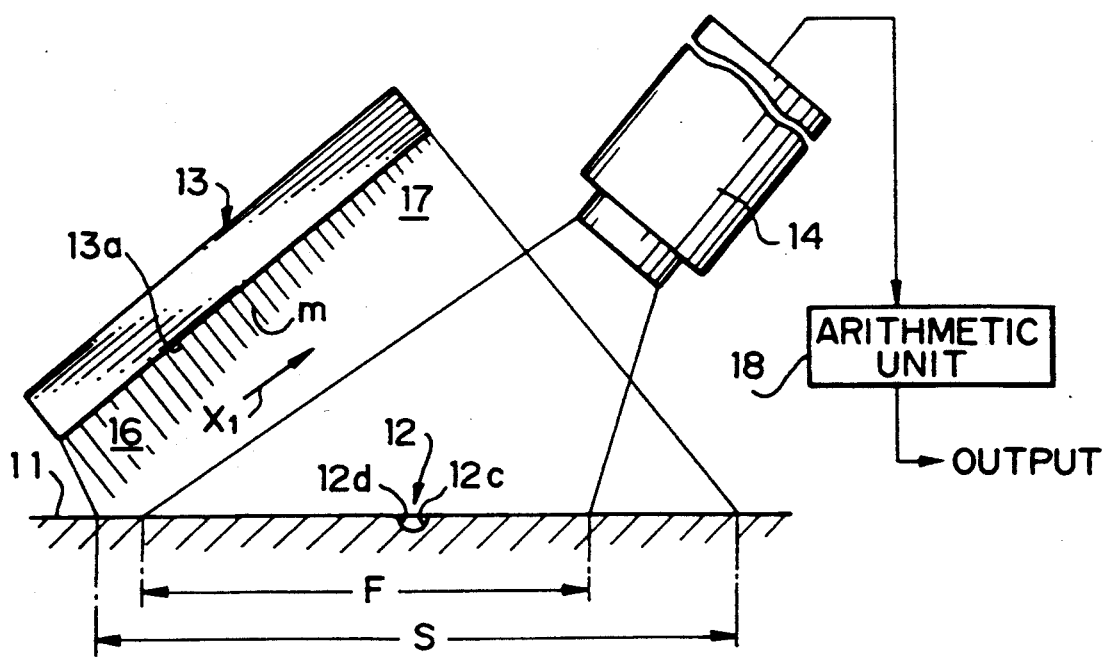

In FIGS. 5A and 5B, a light source 13 as a light radiation means is set so that the luminous intensity (expressed by the length of a line m) of light emerging from a light output surface 13a is changed from high level to low level in a direction indicated by an arrow $X_1$.

As described above, light emerging from the light output surface 13a of the light source 13 is set so that the luminous intensity is uniformly changed in one direction of the output surface 13a, as indicated by the arrow $X_1$, and more particularly, the luminous intensity is gradually decreased along the direction indicated by the arrow $X_1$. An image of the light source 13 is reflected by the inspection surface 11, and is imaged by a video camera 14 as a video signal generation means. In other words, the video camera 14 is arranged to oppose the inspection surface 11 and to be adjacent to the light source 13, so as to have a camera field F which is set so that light emitted from the light source 13 and reflected by the inspection surface 11 can be directly received.

Figure 6A:
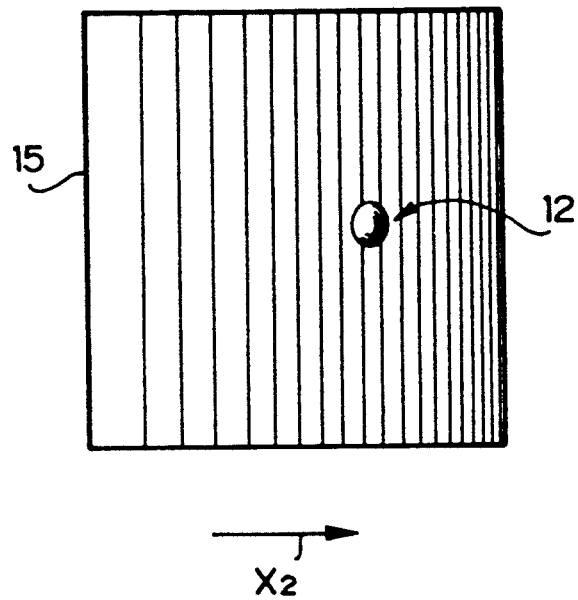
FIGS. 6A and 6B are views showing formation states of images obtained by a camera when convex and concave defects are present on a surface to be inspected, respectively.
Figure 6B:
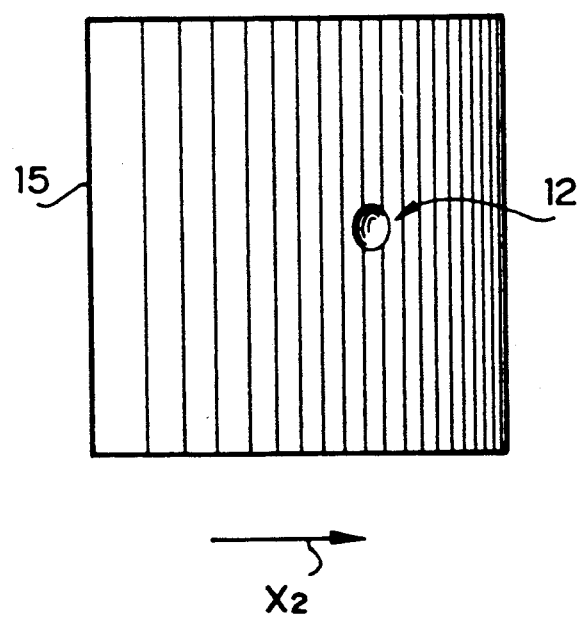
Figure 7A:
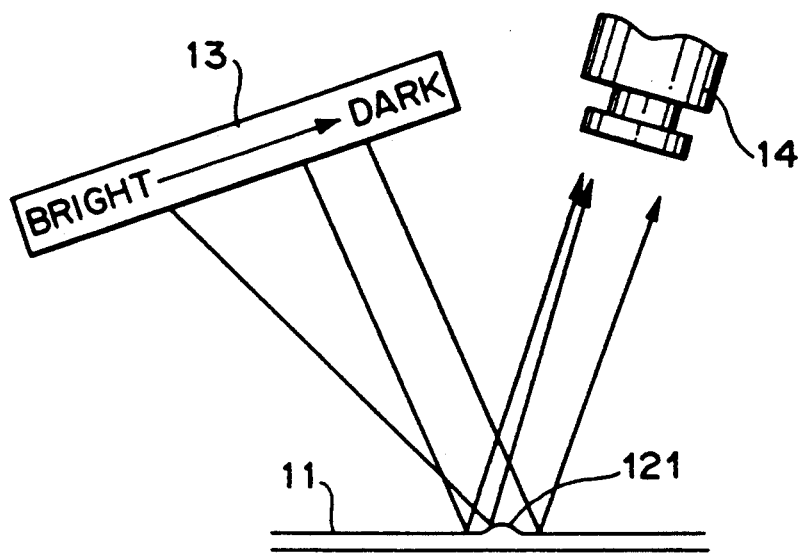
FIGS. 7A and 7B are schematic views showing the incident direction of light when small and large convex defects are present on the surface to be inspected, respectively.
Figure 7B:
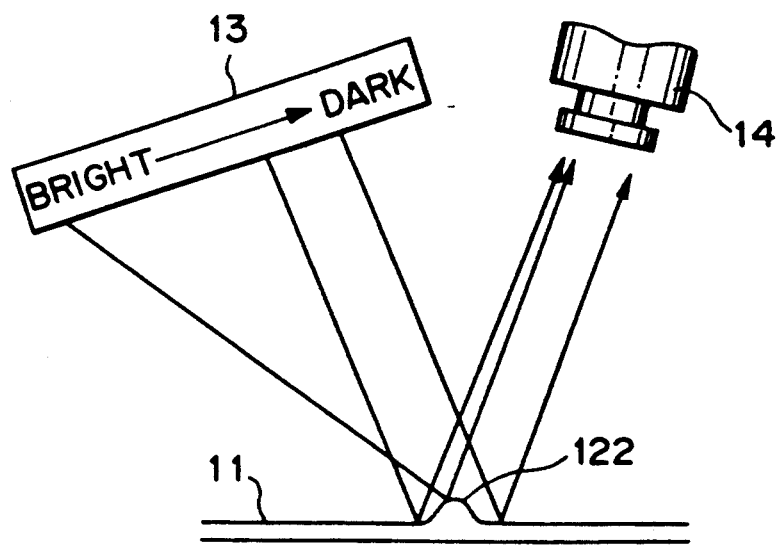

With this arrangement, as shown in FIGS. 6A and 6B, in a received-light image 15 of the video camera 14 which detects light reflected by the inspection surface 11, brightness is changed from high level to low level along a direction indicated by an arrow $X_2$ corresponding to the direction $X_1$ along which the luminous intensity of light emerging from the light output surface 13a of the light source 13 is changed from high level to low level. Note that in FIGS. 6A and 6B, as the density of vertical lines is lower, the brightness becomes higher, and as the density of vertical lines is higher, the brightness becomes lower.

In this state, when a defect portion 12 is formed on the inspection surface 11, the regular reflection direction of light from the light source 13 is changed by the defect portion 12. Upon the change in regular reflection direction of light, a change in brightness of the defect portion 12 becomes different from that of the remaining portion, while the luminous intensity of received light is changed in the direction of the arrow $X_2$ in the received-light image 15 of the video camera 14.

When the defect portion 12 is a convex one, as shown in FIG. 5A, the surface of the defect portion 12 essentially serves as a so-called convex mirror. As a result, on the convex defect portion 12, light from a high-luminous intensity portion 16 of the output surface 13a of the light source 13 is mainly radiated on a surface 12a of the defect portion 12 opposing the output surface 13a according to the reflection theory of the convex mirror, and its regular reflection direction is changed. Light reflected by the defect portion 12 becomes incident on the video camera 14 as object light of the defect portion 12. Note that the focal point of the video camera 14 is adjusted to be on the inspection surface 11 so as to detect a sharp image of the defect portion 12 in the received-light image 15.

Only light from a portion 17 having a relatively low luminous intensity of the output surface 13a is incident on a surface 12b on the rear side of the defect portion 12 when viewed from the output surface 13a. As a result, almost no light reflected by the rear-side surface 12b of the defect portion 12 becomes incident on the video camera 14.

Therefore, in the received-light image 15 of the video camera 14, as shown in FIG. 6A, when the defect portion 12 has a convex shape, the defect portion 12 looks brighter than the remaining portion first, and then looks darker than the remaining portion after the bright portion in the direction of the arrow $X_2$, which is directed from a bright portion toward a dark portion of the received-light image 15 of the video camera 14.

The brightness of the defect portion 12 in the received-light image of the video camera 14 is changed depending on the height and the curve pattern (an inclination angle defined between a plane contacting the outer surface at a reflection point and the inspection surface 11) of the outer surface of the defect portion 12. For example, if the defect portion 12 is a convex portion 121 having a small height (FIG. 7A), its inclination is moderate (small inclination angle), and the incident angle (at one side 12a) of light which is regularly reflected at one side 12a on the side of the light source 13 and becomes incident on the video camera 14 is small. As a result, the brightness on one side 12a of the defect portion 12 is relatively high. Similarly, the brightness on the other side 12b of the convex portion 121 is relatively low.

On the other hand, when the defect portion 12 is a convex portion 122 having a large height (FIG. 7B), its inclination becomes steep (large inclination angle), and the incident angle (at one side 12a) of light which is regularly reflected at one side 12a on the other side of the light source 13 and becomes incident on the video camera 14 is large. As a result, the brightness on one side 12a is very high. Similarly, the brightness on the other side 12b of the convex portion 122 is very low.

Therefore, a change in brightness of the defect portion 12 in the received-light image 15 of the video camera 14 can be analyzed to detect the height of the defect portion 12.

Figure 8:
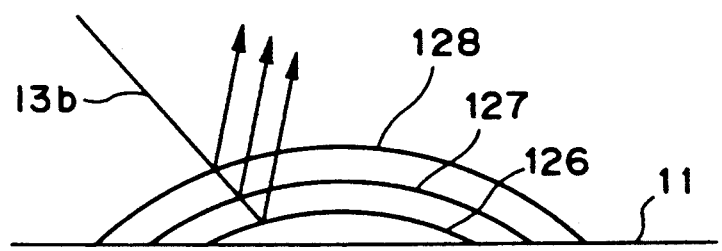
FIG. 8 is an explanatory view of a state wherein a regular reflection angle of light is determined according to curve patterns of surface defects.

In this case, when convex portions 126, 127, and 128 having different heights have the same curve pattern (inclination angle), as shown in FIG. 8, i.e., have different radii of curvature, the incident angles (on the convex portions 126, 127 and 128) of light components 13b which are regularly reflected on one-side portions of these convex portions 126, 127, and 128, and become incident on the video camera 14 are equal to each other. Therefore, when the height is detected, the size (outer diameter) of the defect portion 12 must be analyzed in addition to the change in brightness.

When the defect portion 12 is a concave one, the surface of the defect portion 12 essentially serves as a so-called concave surface. As a result, on the surface of the concave defect portion 12, light from the portion 16 having a high luminous intensity of the output surface 13a of the light source 13 is mainly radiated on a surface 12c of the defect portion 12 far from the output surface 13a, and its regular reflection direction is changed according to the reflection theory of the concave mirror. Some of the light components reflected by the surface 12c are incident on the video camera 14. However, only light from the portion 17 having a relatively low luminous intensity becomes incident on a surface 12d opposite to the surface 12c of the defect portion 12 (i.e., a surface near the output surface 13a), and almost no light from the surface 12d of the defect portion 12 becomes incident on the video camera 14.

Therefore, in the received-light image of the video camera 14, as shown in FIG. 6B, when the defect portion 12 is a concave one, the defect portion 12 looks darker than the remaining portion first, and then looks brighter than the remaining portion after the dark portion in the direction of the arrow $X_2$, which is directed from a bright portion toward a dark portion of the received-light image 15 of the video camera 14.

In this manner, when the defect portion 12 has a recess shape, a change in brightness, and the size (outer diameter) of the defect portion 12 in the received-light image 15 of the video camera 14 are analyzed so as to calculate the depth of the defect portion 12.

The video camera 14 outputs a video signal which changes in accordance with a change in brightness of the received-light image 15. Thereafter, the video signal output from the video camera 14 is input to a video signal arithmetic unit 18. The signal level, on one scanning line near the defect portion 12, of the video signal input to the arithmetic unit 18 forms a waveform shown in FIG. 9A when the defect portion 12 has a convex shape, or forms a waveform shown in FIG. 9B when it has a concave shape.

The video signal is subjected to differential processing in the arithmetic unit 18, and thereafter, its absolute value is calculated.

Figure 9A:
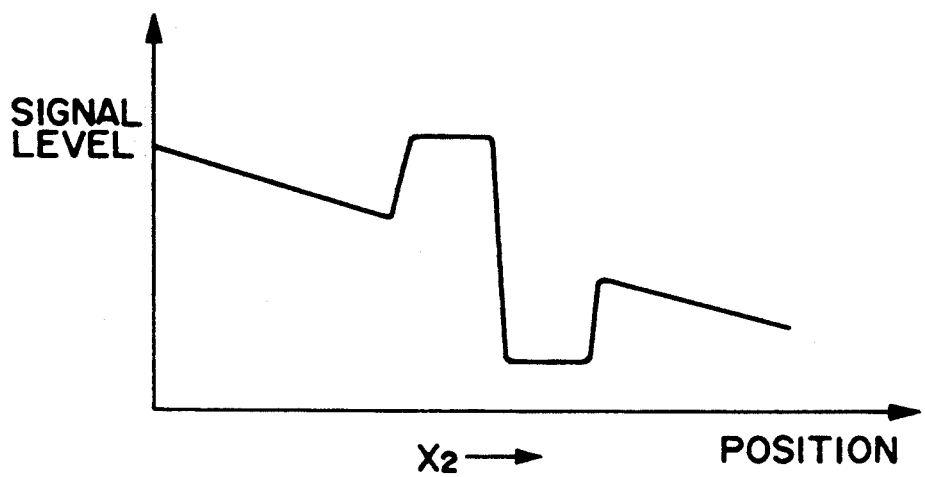
FIGS. 9A and 9B are graphs showing changes in signal level on one scanning line of a video signal near a portion where a defect portion is present.
Figure 9B:
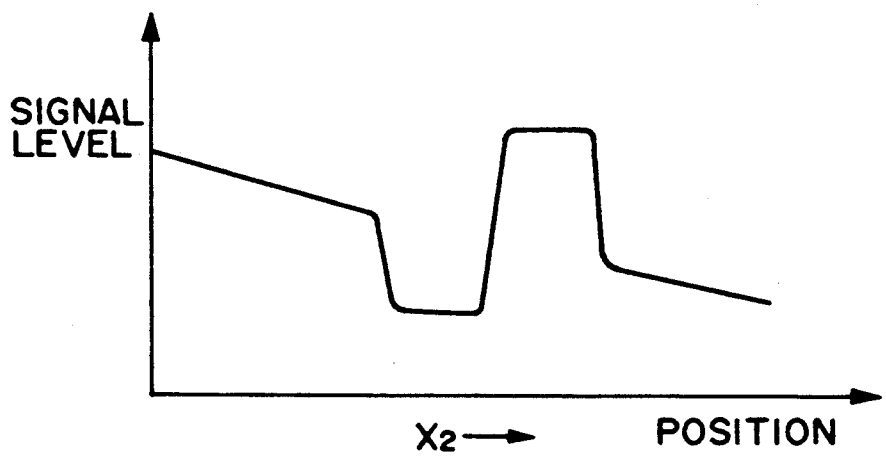
Figure 10:
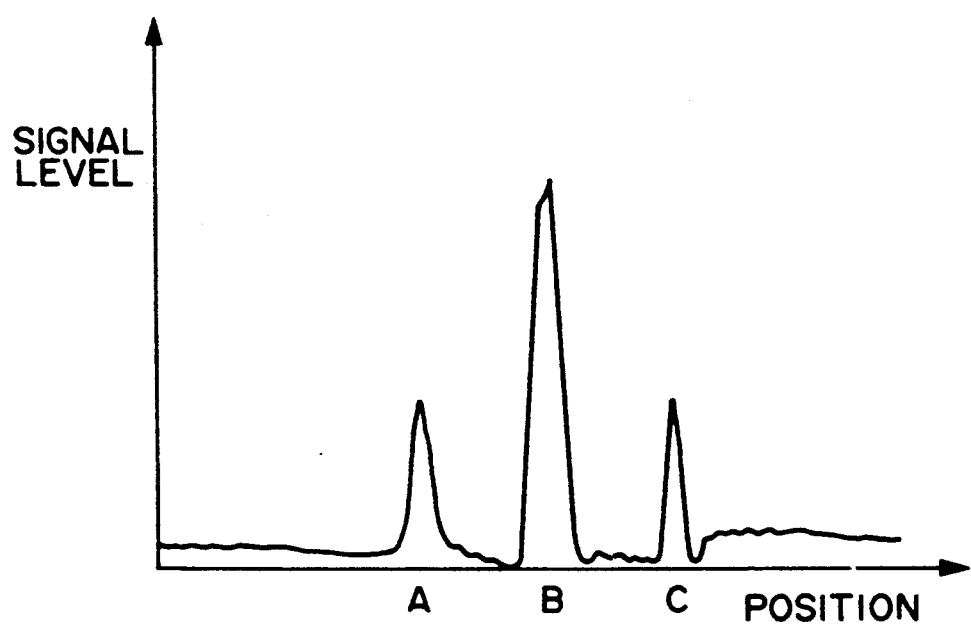
FIG. 10 is a graph showing a signal waveform after the video signal shown in FIGS. 9A and 9B is subjected to differential processing and absolute value processing.

Therefore, the video signals having the signal levels shown in FIGS. 9A and 9B are converted into a signal having three peaks, as shown in FIG. 10. Of these three peaks, peaks A and C represent outer-diameter portions of the defect portion 12. A peak B represents a portion where the signal level is largely changed in a region of the defect portion 12. On the basis of these peaks A and C, the position of the surface defect, and the size (outer diameter) of the defect portion 12 can be detected.

In the arithmetic unit 18, the brightness of the defect portion 12 in the received-light image is detected on the basis of the signal level of the video signal at the position of the defect portion 12, and the height (depth) of the defect portion 12 is calculated using the detected brightness and the size (outer diameter) of the defect portion 12 obtained as described above.

The detected position and height (depth) data of the defect portion 12 are output from the arithmetic unit 18, and are supplied to a predetermined defect portion processing apparatus, or the like.

The structure of a first embodiment of the surface defect inspection apparatus using the above-mentioned operation principle will be described in detail below with reference to FIGS. 11 and 12.

Figure 11:
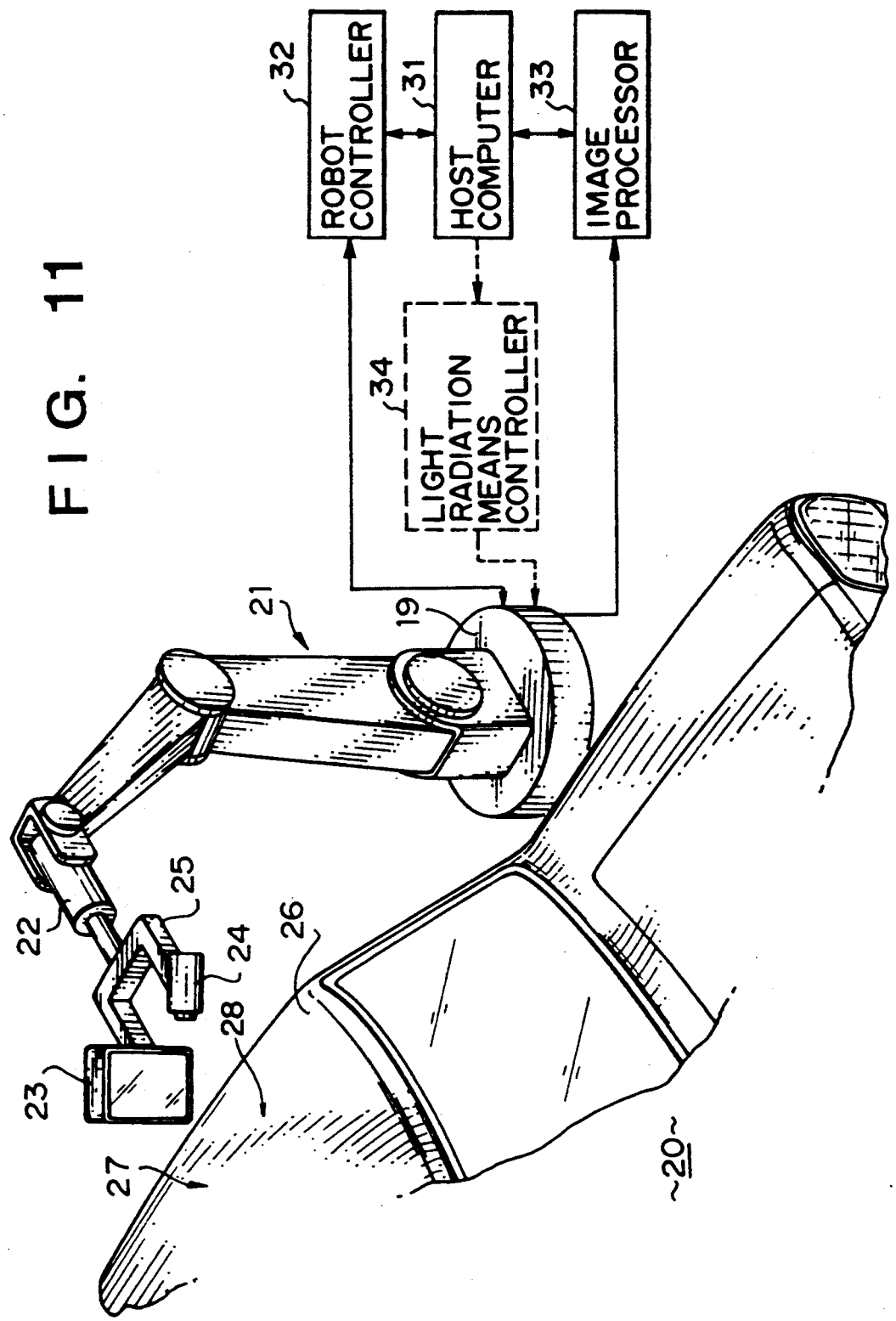
FIG. 11 is a perspective view showing the structure of the surface defect inspection apparatus according to the first embodiment of the present invention, which is applied to a painting defect inspection apparatus for a vehicle body.

A painting inspection station 20 for a vehicle body is equipped with an inspection robot apparatus 21 which is mounted on a base 19, and serves as a painting defect inspection apparatus for inspecting a painted surface 27 of a conveyed vehicle body 26, and detecting the presence/absence of a painting defect portion 28, as shown in FIG. 11.

The robot apparatus 21 comprises a distal end arm 22 which is movable to an arbitrary position, and can have an arbitrary posture. A light radiation mechanism 23 corresponding to the above-mentioned light source 13 (FIGS. 5A and 5B), and a CCD camera 24 corresponding to the above-mentioned video camera 14 (FIGS. 5A and 5B) are mounted on the distal end of the distal end arm 22 via a support metal member 25. The light radiation mechanism 23 and the CCD camera 24 mounted on the robot apparatus 21 trace the painted surface 27 (corresponding to the inspection surface 11 shown in FIGS. 5A and 5B) of the vehicle body 26 conveyed in the painting inspection station 20. In this case, light radiated from the light radiation mechanism 23 is reflected by the painted surface 27 of the vehicle body 26, and becomes incident on the CCD camera 24. In other words, the positional relationship between the light radiation mechanism 23 and the CCD camera 24 is determined so that the light radiation mechanism 23 is mainly projected in a received-light image 15 of the CCD camera 24 via the painted surface 27 serving as a mirror surface.

In the painting defect inspection apparatus (inspection robot apparatus) 21 comprising the light radiation mechanism 23 and the CCD camera 24, the driving operation of a robot controller 32 is controlled in accordance with an instruction supplied from a host computer 31, and the robot apparatus 21 is driven by the robot controller 32.

The robot apparatus 21 moves the light radiation mechanism 23 and the CCD camera 24 to trace the surface of the vehicle body 26 upon operation of an internal actuator (not shown), and outputs a video signal obtained by the CCD camera 24 to an image processor 33.

As described above, the image processor 33 amplifies the video signal, and then differentiates the amplified video signal. A scanning line of the video signal, where the differentiated signal exceeds a predetermined threshold value, is detected and a timing on the detected scanning line is detected. These data are supplied to and analyzed by the host computer 31. With this analysis, the coordinate position of the painting defect portion 28, and whether the painting defect portion 28 has a convex or concave shape are detected.

Then, data representing a brightness level of the painting defect portion 28 in the video signal, and data indicating the size of the painting defect portion 28 and whether the portion 28 has a convex or concave shape are supplied to and analyzed by the host computer 31, thereby calculating the height (or depth) of the painting defect portion 28.

On the basis of the detection result obtained as a result of the above-mentioned data processing, a repair according to the three-dimensional pattern of the painting defect portion 28 present on the painted surface of the vehicle body 26 is performed. In the repair work, when the defect portion 28 has a convex shape, the projecting portion is cut in a small range. On the other hand, when the painting defect portion 28 has a concave shape, the paint layer is cut in a relatively wide range including the painting defect portion 28.

The repair can be manually performed. However, in general, the repair is automatically performed by the above-mentioned robot apparatus 21 or another repair robot apparatus (not shown).

Figure 12:
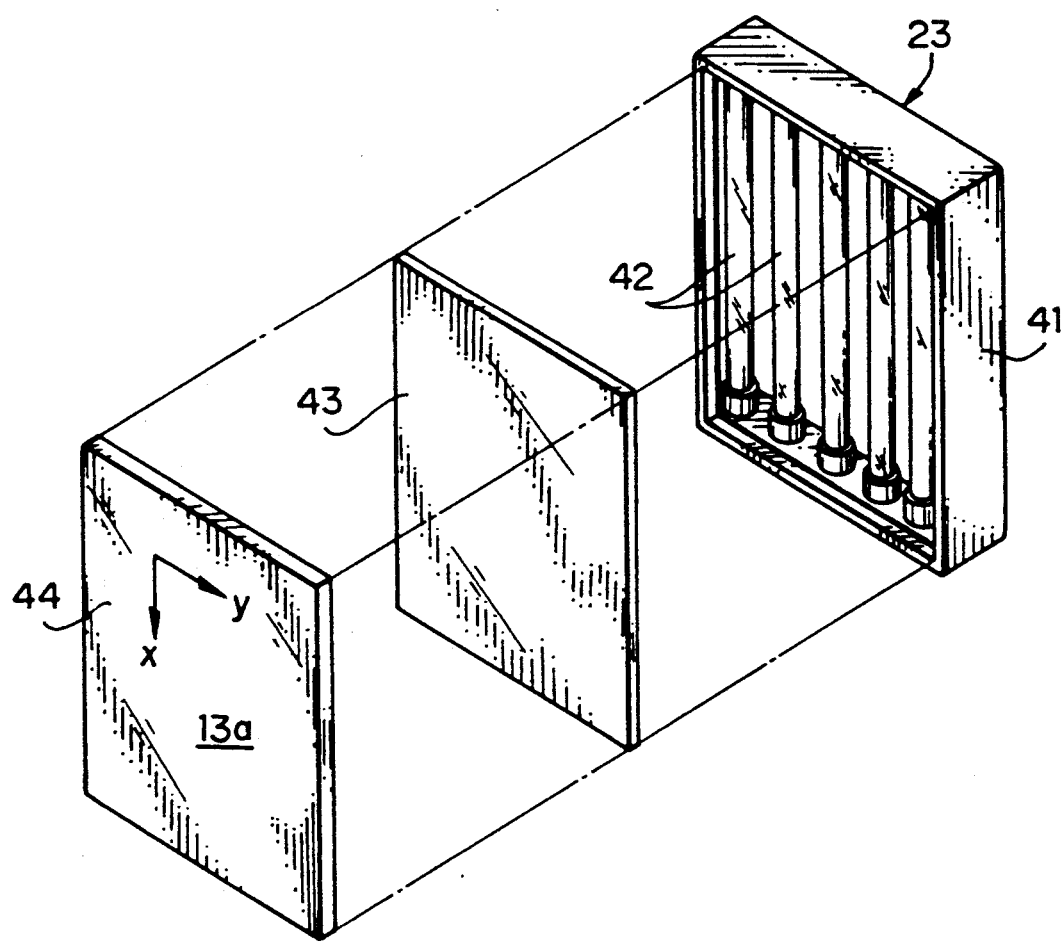
FIG. 12 is an exploded perspective view of the structure of a light radiation mechanism shown in FIG. 11.

The light radiation mechanism 23 is constituted by a box 41 having one open side surface opposing the painted surface 27, and a plurality of fluorescent lamps 42 (the present invention is not particularly limited to the fluorescent lamps 42) arranged inside the box 41, as shown in FIG. 12. An optical filter 43 is arranged on the open side surface of the box 41, and a diffusion screen 44 is mounted to cover the entire surface of the optical filter 43.

The optical filter 43 uniformly changes a luminous intensity distribution of light emitted from the fluorescent lamps 42 in one direction of the light output surface 13a defined by the surface of the diffusion screen 44. More specifically, the optical filter 43 is set so that points having the same x-coordinate value on the x-y coordinate system set on the light output surface 13a, as shown in FIG. 12, have the same light transmittance value, and points having different y-coordinate values have different light transmittance values according to the y-coordinate values. Thus, a light radiation region S (FIGS. 5A and 5B) where an illuminance is changed in one direction is formed on the painted surface 27 of the vehicle body 26, as shown in FIG. 11.

The diffusion screen 44 diffuses light transmitting through the optical filter 43 so as not to form regions having a low luminous intensity on portions of the output surface 13a corresponding to portions between the adjacent fluorescent lamps 42 when the fluorescent lamp 42 are arranged at given intervals.

Note that a light radiation mechanism controller 34 may be arranged, as indicated by a dotted line in FIG. 11, and a change (gradient) in luminous intensity provided to the light radiation mechanism 23 may be defined by changing application voltages to the fluorescent lamps 42 by the light radiation mechanism controller 34. In this case, the optical filter 43 can be omitted.

In the painting defect inspection apparatus with the above-mentioned structure, when the painted vehicle body 26 is conveyed into the painting inspection station 20, a painting defect inspection operation is started. More specifically, under the control of the robot controller 32, the robot apparatus 21 moves the light radiation mechanism 23 and the CCD 24 to trace the surface pattern of the vehicle body 26 while maintaining a predetermined positional relationship between the light radiation mechanism 23 and the CCD camera 24, and a proper distance between the light radiation mechanism 23 and the CCD camera 24, and the surface of the vehicle body 26.

In this case, as has been described above with reference to FIGS. 5A and 5B, an optical image, reflected by the painted surface 27 serving as the mirror surface, of the light output surface 13a where a luminous intensity distribution is uniformly changed in one direction, is projected in the camera field F. That is, the CCD camera 24 forms the received-light image 15 whose brightness is uniformly changed in correspondence with the luminous intensity distribution of the light radiation mechanism 23.

Therefore, when the painting defect portion 28 is formed on the painted surface 27, the regular reflection direction of light emitted from the light source 13 is changed at that portion. As has been described in the description of the principle with reference to FIGS. 5A and 5B, and FIGS. 6A and 6B, for example, when the painting defect portion 28 has a convex shape, a portion, corresponding to the painting defect portion 28, of the received-light image 15 of the CCD camera 24 looks brighter than the remaining portion, and then looks darker than the remaining portion after the bright portion along the direction $X_2$ in which the brightness of the received-light image 15 is changed from high level to low level, as shown in FIG. 6A.

When the painting defect portion 28 has a concave shape, a portion, corresponding to the painting defect portion 28, of the received-light image 15 of the CCD camera 24 looks darker than the remaining portion, and then looks brighter than the remaining portion after the dark portion along the direction $X_2$ in which the brightness of the received-light image 15 is changed from high level to low level, as shown in FIG. 6B.

The CCD camera 24 outputs a video signal which changes according to a change in brightness of the received-light image 15 to the image processor 33.

Upon reception of the video signal, the image processor 33 detects the scanning line of the video signal where the differentiated signal of the video signal output from the CCD camera 24 exceeds a predetermined threshold value on the basis of the presence of the painting defect portion 28, a timing at which the differentiated signal exceeds the threshold value on the detected scanning line, and a change in sign of the differentiated signal near the detected timing. According to the detection results, the position and size of the painting defect portion 28 in the received-light image 15, and the three-dimensional pattern of the painting defect portion 28 are detected. These detection data, and the position of the distal end arm 22 of the robot apparatus 21 are stored in a memory. When the painting defect portion 28 is to be repaired, the storage content of the memory is read out, and the repair of the painting defect portion 28 is performed, as described above.

In this manner, the painting defect portion 28 is repaired on the basis of the obtained height (depth) data of the painting defect portion 28. Therefore, according to the painting defect inspection apparatus of the first embodiment, the painting defect portion 28 can be precisely and quickly repaired.

The present invention is not limited to the arrangement of the above embodiment, and various changes and modifications may be made within the spirit and scope of the invention.

For example, in the first embodiment described above, the surface defect inspection apparatus is applied to detection of a painting defect portion of a painted surface of a vehicle body. However, the present invention is not limited to this, but may be applicable to various other applications as long as a defect formed on a surface serving as a mirror surface is to be inspected.

In the first embodiment described above, the luminous intensity of light emerging from the light output surface 13a of the light source 13 is uniformly changed. However, the present invention is not limited to this. For example, the wavelength of light emerging from the light output surface 13a of the light source 13 may be uniformly changed, as will be described in a second embodiment hereinafter.

A surface defect inspection apparatus of the second embodiment will be described in detail below with reference to FIGS. 13A through 16. In the following description, the same reference numerals denote the same parts as in the first embodiment described above, and a detailed description thereof will be omitted.

The operation principle of the second embodiment will be described below with reference to FIGS. 13A through 14B.

FIG. 13A shows a case wherein an inspection surface 11 has a convex defect portion 12, and FIG. 13B shows a case wherein the inspection surface 11 has a concave defect portion 12.

In FIGS. 13A and 13B, a light source 50 as a light radiation means is set so that the wavelength of light emerging from a light output surface 50a is changed in a predetermined order in one direction indicated by an arrow $X_1$ of the output surface 50a, i.e., the wavelength is gradually increased in a visible light region along the direction of the arrow $X_1$. In other words, the light source 50 has the output surface 50a for outputting light to have a predetermined color pattern which changes along the above-mentioned direction $X_1$. That is, the output surface 50a is divided into a first output region A, a second output region B, a third output region C, . . . along the direction of the arrow $X_1$. The respective output regions output light components in different colors in a predetermined order so that the wavelength is gradually increased in a visible light region. For example, the first output region A outputs light in a color (e.g., violet) having the shortest wavelength in the visible light region, the second output region B outputs light in a color (e.g., bluish violet) having a wavelength slightly longer than violet, the third output region C outputs light in a color (e.g., blue) having a wavelength slightly longer than bluish violet, and the last output region Z located on the side opposite to the first output region A outputs light in a color (e.g., red) having the longest wavelength in the visible light region.

Figure 14A:
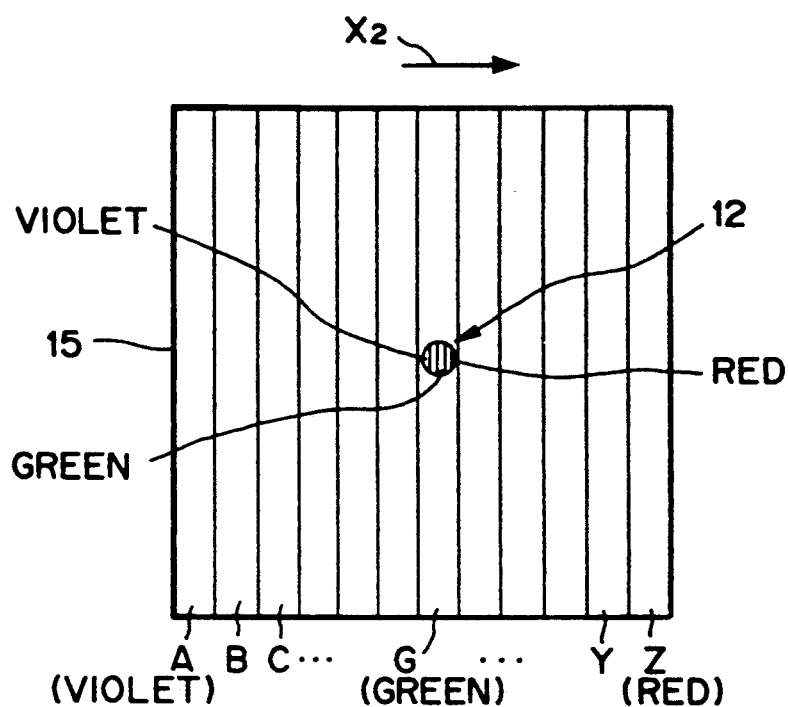
FIGS. 14A and 14B are views showing formation states of images obtained by a camera when convex and concave defects are present on a surface to be inspected, respectively.
Figure 14B:
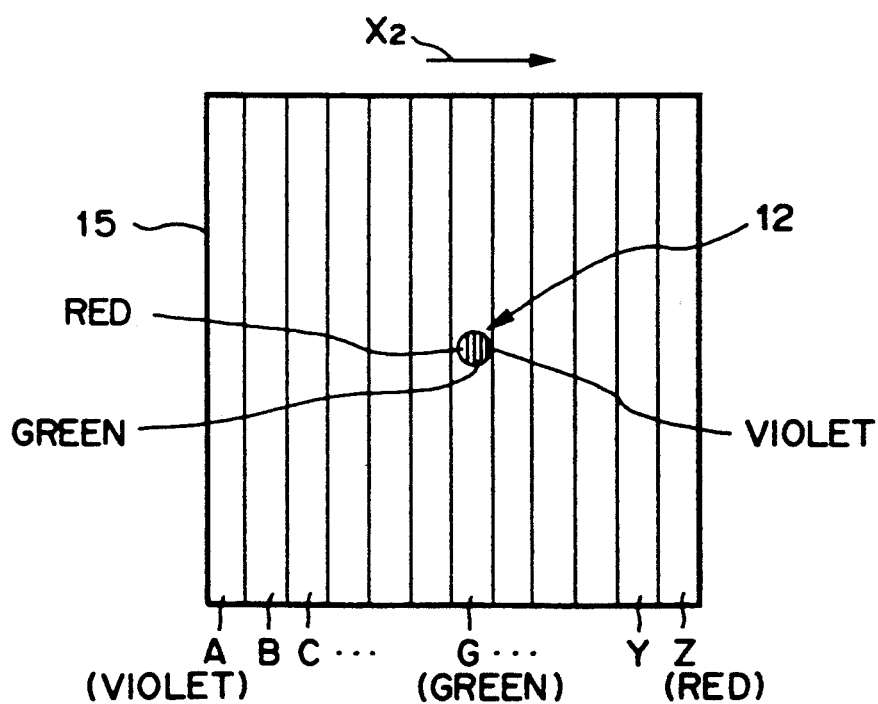

An image of the light source 50 reflected by an inspection surface 11 is detected in a camera field F of a color video camera 54. More specifically, the light output surface 50a of the light source 50 is directly projected as a received-light image 15 of the color video camera 54, as shown in FIGS. 14A and 14B. As a result, an image whose color is sequentially changed along the direction of an arrow $X_2$ is formed as the received-light image 15 in correspondence with the color pattern in which the colors of light components output from the output surface 50a are sequentially changed in turn from violet along the direction of the arrow $X_1$.

In this state, when a defect portion 12 is formed on the inspection surface 11, the regular reflection direction of light from the light source 50 is changed at that portion, and the color pattern of the output surface 50a reflected by the inspection surface 11 is disordered. The defect portion 12 can be discriminated by the disordered color pattern as follows.

More specifically, when the defect portion 12 has a convex shape, as shown in FIG. 13A, the surface of the defect portion 12 serves as a so-called convex mirror. As a result, of light components from the output surface 50a of the light source 50, light components from the first output region A (region for outputting light having a short wavelength) located on the trailing end side of the direction of the arrow $X_1$, e.g., violet light components are mainly radiated on a surface 12a of the convex defect portion 12, which surface opposes the output surface 50a, and the regular reflection direction of these light components is changed according to the reflection theory of the convex mirror. Then, some light components become incident on the video camera 54.

Therefore, in a portion, corresponding to the defect portion 12, of the received-light image 15 of the color video camera 54, as shown in FIG. 14A, when the defect portion 12 has a convex shape, an image having a color pattern whose wavelength is sequentially increased from a short-wavelength light component along the direction of the arrow $X_2$ in accordance with the color pattern of light components emerging from the output surface 50a, is independently projected in a reduced scale on, e.g., a green region.

On the other hand, when the defect portion 12 has a concave shape, as shown in FIG. 13B, the surface of the defect portion 12 serves as a so-called a concave mirror. As a result, of light components from the output surface 50a of the light source 50, light components from the last output region Z (region for outputting light having a long wavelength) located on the leading end side of the direction of the arrow $X_1$, e.g., red light components are mainly radiated on a surface 12b of the convex defect portion 12, which surface opposes the output surface 50a, and the regular reflection direction of these light components is changed according to the reflection theory of the convex mirror. Then, some light components become incident on the video camera 54.

Therefore, in a portion, corresponding to the defect portion 12, of the received-light image 15 of the color video camera 54, as shown in FIG. 14B, when the defect portion 12 has a concave shape, an image having a color pattern whose wavelength is sequentially decreased from a long-wavelength light component along the direction of the arrow $X_2$ in accordance with a reversed order to that of the color pattern of light components emerging from the output surface 50a, is independently projected in a reduced scale on, e.g., a green region.

In this manner, the color pattern on the output surface 50a of the light source 50 not resembling colors of the light components originally incident on the light-receiving surface of the color video camera 54 is focused in a reduced scale. As a result, the presence (position) of the defect portion 12 is detected. When the change direction of the reduced color pattern along the direction of the arrow $X_2$ is the same as the direction of the arrow $X_1$ on the output surface 50a, the convex defect portion 12 is detected; otherwise, the concave defect portion 12 is detected.

The position and three-dimensional pattern of the defect portion 12 according to the above-mentioned principle are discriminated on the basis of chrominance signals included in a video signal from the color video camera 54 by an image processor to be described later.

- The arrangement of the second embodiment using the above-mentioned principle will be described below with reference to FIGS. 15 and 16.

The arrangement of the second embodiment is substantially the same as that of the first embodiment described above, except for a light radiation mechanism 52 corresponding to the light source 50 for outputting light having a predetermined color pattern, and the color video camera 54 serving as a color scanner for discriminating colors in units of pixels constituting the received-light image 15, and outputting chrominance signals corresponding to the respective colors. An image processor 33 detects a scanning line where the predetermined color pattern of light emerging from the light radiation mechanism 52 is present in a reduced scale in a color (e.g., green) of originally incident light in the received-light image 15 (FIGS. 14A and 14B) of the color video camera 54, and a detection timing on the detected scanning line on the basis of the chrominance signals included in a video signal input from the color video camera 54. The data are sent to and analyzed by a host computer 31. Thus, the coordinate position of the defect portion 12 is detected, and whether a painting defect portion 28 has a convex or concave shape is detected on the basis of a change direction of the detected color pattern.

According to the detection results, the repair according to the three-dimensional pattern of the painting defect portion 28 present on a painted surface 27 of a vehicle body 26 is performed.

Figure 16:
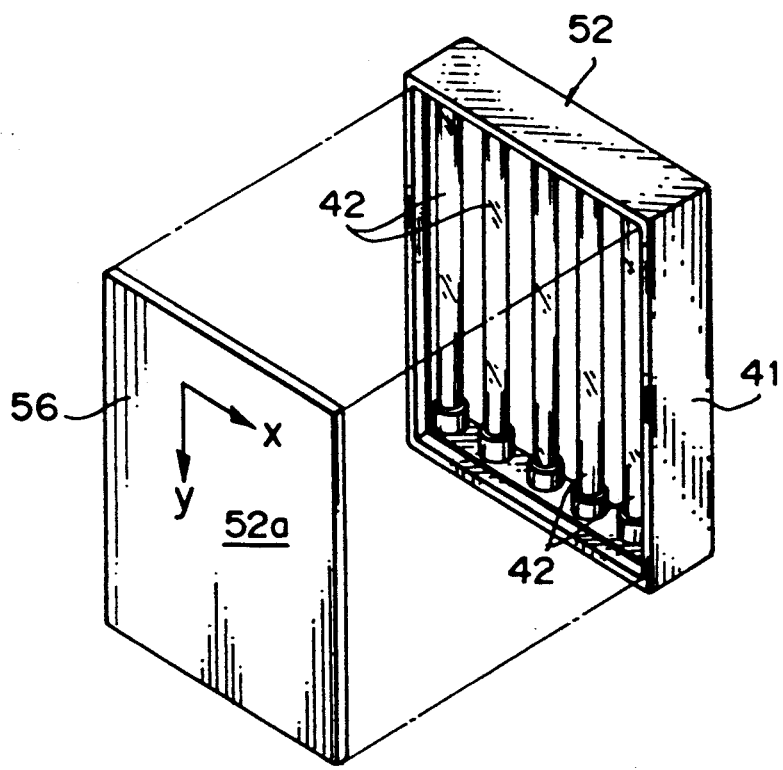
FIG. 16 is an exploded perspective view of the structure of a light radiation mechanism shown in FIG. 15.

In the light radiation mechanism 52, as shown in FIG. 16, an optical filter 56 is mounted to close an open surface of a box 41 unlike in the first embodiment.

The filter 56 is formed to output light having a predetermined color pattern in which the wavelengths of colors of light emitted from fluorescent lamps 42 are sequentially increased in the order of, e.g., violet, bluish violet, blue, . . . , in one direction of the light output surface 50a formed by the optical filter 56. With this optical filter 56, light components have the same color at points having the same x-coordinate value on the x-y coordinate system set on the light output surface 50a, as shown in FIG. 16, and light components value have different colors at points having different y-coordinate values.

In the painting defect inspection apparatus of the second embodiment with the above-mentioned arrangement, the wavelength is sequentially changed along the direction $X_1$ in place of the luminous intensity in the first embodiment described above, so that the position of the painting defect portion 28 present on the painted surface 27, and its formation state, i.e., whether the defect portion 28 has a concave or convex shape can be detected.

Figure 17A:
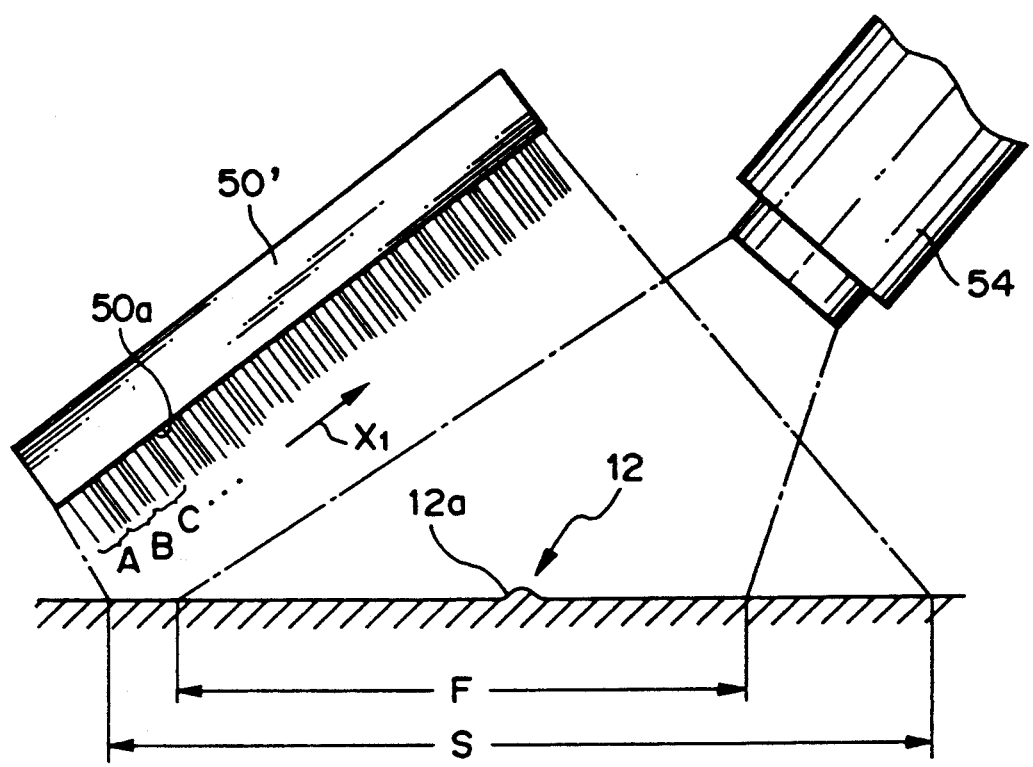
FIGS. 17A and 17B are views showing a structure of a first modification of the second embodiment.
Figure 17B:
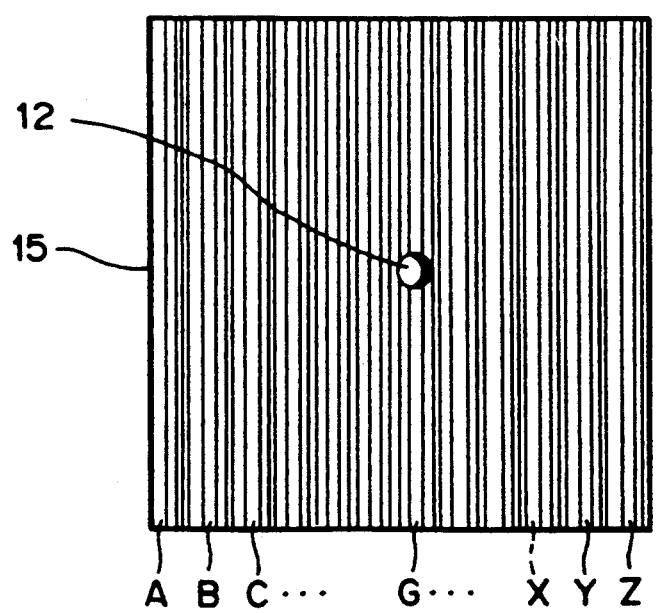

The second embodiment is not limited to the above arrangement. For example, as shown in FIGS. 17A and 17B as the first modification of the second embodiment, light components of the respective colors emerging from the light output surface 50a of the light source 50' may have a luminous intensity gradient (e.g., 256 gradation levels). In FIGS. 17A and 17B, as the density of lines in each region becomes lower, the luminous intensity becomes higher, and as it becomes higher, the luminous intensity becomes lower.

According to the arrangement of the first modification, in the received-light image 15 of the color video camera 54, the brightness of colors of light incident from the painting defect portion 28 is changed in accordance with the position of the painting defect portion 28, as has been described above in the first embodiment. Thus, the painting defect portion 28 can be more easily detected.

In the second embodiment, a defect portion 12 is detected by the image processor 33. Alternatively, a defect portion 12 may be detected by monitoring a video signal from the video camera 54 by an inspector on a monitor television, and data such as a pattern, position, and the like of the defect portion may be stored in a recording device.

In the second embodiment, the light radiation mechanism 52 radiates light in the visible light region. However, the present invention is not limited to this. For example, light outside the visible light region may be output. In addition, the color pattern need not be changed so that the wavelength is sequentially increased, but may be changed so that the wavelength is sequentially decreased. Furthermore, the color pattern may be set so that colors are changed in an arbitrary order regardless of the wavelength.

In each of the first and second embodiments, an image of the light radiation mechanism 23 or 52 is formed to have a luminous intensity or wavelength distribution obtained by changing a luminous intensity or wavelength of light emerging from the output surface in one direction, and is reflected by the painted surface 27 serving as a mirror surface. The reflected image is imaged by the video camera 24 or 54, and the imaging result is processed by the image processor 33, thereby detecting the position of the painting defect portion 12 formed on the painted surface 27, and its formation state (i.e., whether the portion 12 has a concave or convex shape). However, the present invention is not limited to this. For example, the output surface of the light radiation mechanism may output light having a luminous intensity distribution in which the luminous intensity level is repetitively changed, as will be described in a third embodiment below.

The arrangement of a surface defect inspection apparatus according to the third embodiment of the present invention will be described in detail below with reference to FIGS. 18 through 22.

The operation principle of the third embodiment will be described below with reference to FIGS. 18 and 19.

Figure 18:
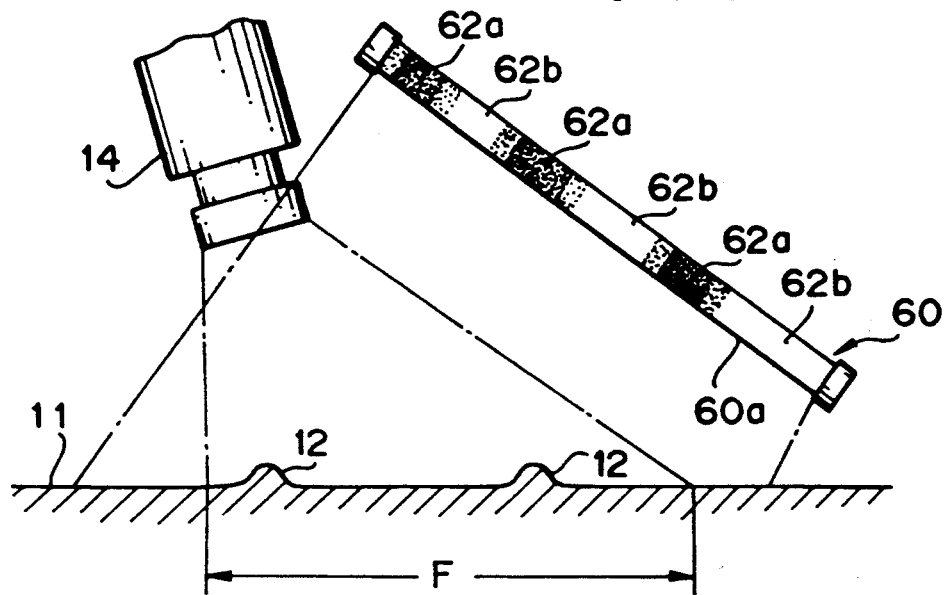
FIG. 18 is an explanatory view for explaining the operation principle of a surface defect inspection apparatus according to a third embodiment of the present invention.

In FIG. 18, a light source 60 as a light radiation means has a wide output surface 60a, and radiates light on an inspection surface 11 over a wide range. Portions 62a having a low luminous intensity, and portions 62b having a high luminous intensity are alternately arranged on the output surface 60a of the light source 60, so that high- and low-level portions repetitively appear in the luminous intensity distribution. The luminous intensity of a boundary between the adjacent portions 62a and 62b is smoothly changed. A camera 14 as an imaging means is arranged adjacent to the light source 60. The camera 14 images the light source 60 via the inspection surface 11 serving as a mirror surface.

Since high-level and low-level portions alternately appear in the luminous intensity distribution of the light source 60, the light-receiving surface of the camera 14 for detecting reflected light of the light radiation region receives a reflected image whose light amount is changed accordingly, and an image including bright and dark portions corresponding to the luminous intensity distribution of the light source 60 is formed as the received-light image. FIG. 19 shows the received-light image 15. In FIG. 19, reference numeral 64a denotes a dark portion; and 64b, a bright portion.

As described above, the inspection surface 11 serves as a mirror surface, and a defect portion 12 formed on the inspection surface 11 also serves as a mirror surface. In the third embodiment, the defect portion 12 is assumed to have a moderate convex curved surface. As a result, the defect portion 12 serves as a so-called convex mirror. On the surface (curved surface) of the defect portion 12, regular reflection occurs in a direction different from that on the inspection surface 11 excluding the defect portion 12. Therefore, the light source 60 having the luminous intensity distribution including high-level and low-level portions is projected in a reduced scale on the surface of the defect portion 12. More specifically, a change in luminous intensity of reflected light corresponding to the luminous intensity distribution of the light source 12 is formed on the defect portion 12, and adjacent regions 66a and 66b respectively having low and high luminous reflection intensity levels form a light reflection surface as a whole. Light reflected by the defect portion 12 serves as object light of the defect portion 12. The light-receiving surface of the camera 14 for receiving reflected light (i.e., object light) by the defect portion 12 also receives reflected light whose light amount is changed according to the above-mentioned distribution, and an image including bright and dark portions corresponding to the luminous intensity distribution of the light source 60 is formed as an image of the defect portion 12.

In this state, a surface defect of the inspection surface 11 is inspected. In the surface defect inspection, if a defect portion 12 is formed on a portion of the inspection surface 11, which portion reflects an image of the region 62a having a low luminous intensity (a region corresponding to the dark portion 64a in the received-light image) of the light source 60, regular reflection in a direction different from that of the remaining portion occurs on the defect portion 12. As described above, object light having the adjacent regions 66b and 66a respectively having high and low reflection luminous intensity levels is incident on the light-receiving surface of the camera. For this reason, as the received-light image 15, the defect portion 12 in which the bright and dark portions 66b and 66a are alternately present adjacent to each other in the dark portion 64a is projected. In this manner, the bright portion 66b of the defect portion 12 is projected as a white dot in the dark portion 64a.

If a defect portion 12 is formed on a portion of the inspection surface 11, which portion reflects an image of the region 62b having a high luminous intensity (a region corresponding to the bright portion 64b in the received-light image) of the light source 60, regular reflection in a direction different from that of the remaining portion similarly occurs on the defect portion 12. For this reason, the defect portion 12 in which the bright and dark portions 66b and 66a are alternately present adjacent to each other in the bright portion 64a is projected as the received-light image 15. In this manner, the dark portion 66a of the defect portion 12 is projected as a black dot in the bright portion 64b.

Therefore, even when the inspection surface is irradiated with light over a two-dimensional wide range, the defect portion 12 can be detected as a clear image having a difference in brightness from the surrounding portion. Therefore, even a small defect portion 12 can be reliably detected.

The same as in the case of the convex defect portion applies to a case wherein the defect portion 12 is defined by a concave curved surface.

Figure 20:
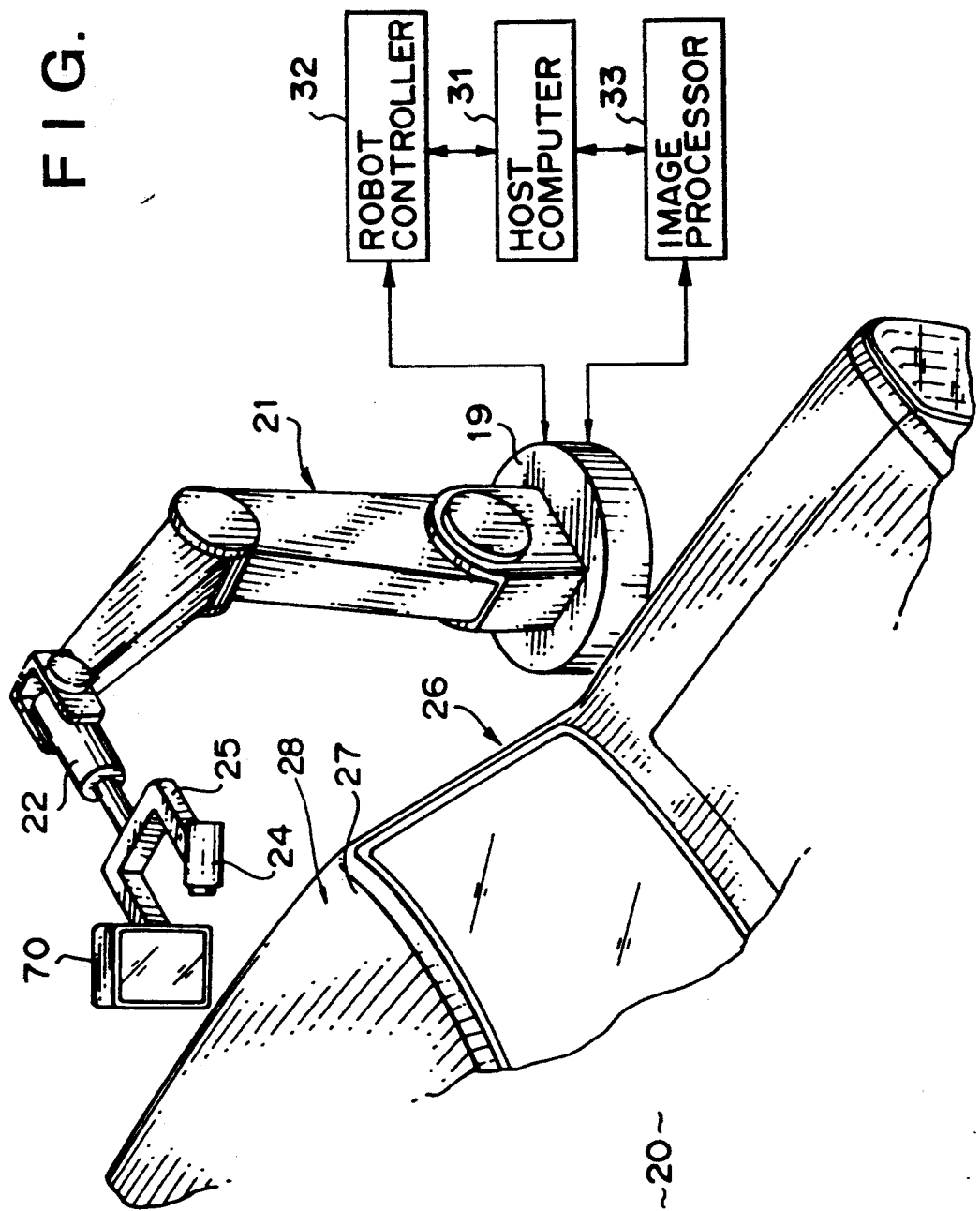
FIG. 20 is a perspective view showing a structure of a surface defect inspection apparatus according to the third embodiment of the present invention, which is applied to a painting defect inspection apparatus for a vehicle body.
Figure 21:
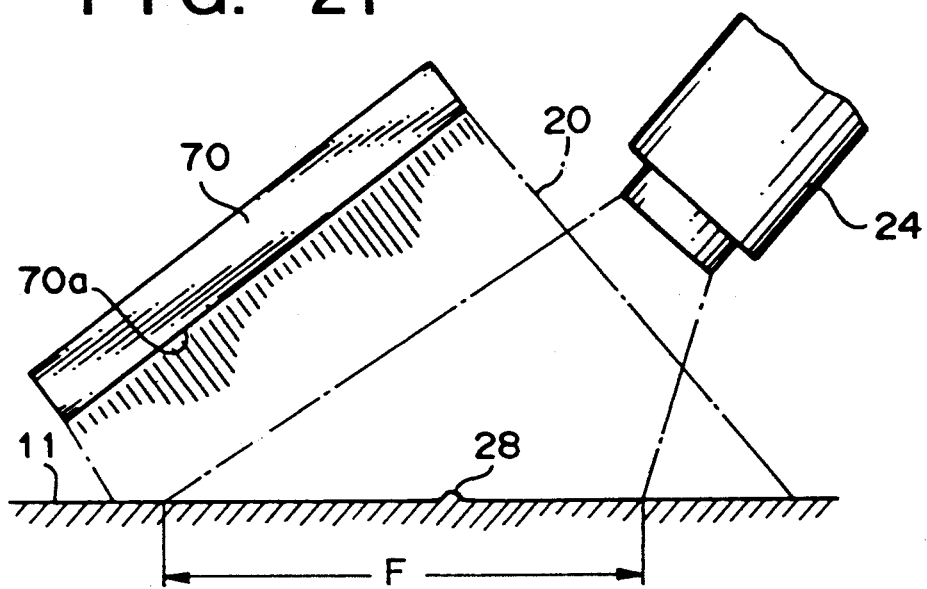
FIG. 21 is a view showing a state wherein an image of a light radiation mechanism reflected by a painted surface is imaged by a camera.

The arrangement of the third embodiment of the surface defect inspection apparatus using the above-mentioned principle, which is applied to a painting defect inspection apparatus for inspecting a painted surface of a vehicle body, will be described below with reference to FIGS. 20 through 22.

The arrangement of the third embodiment is substantially the same as the first embodiment, except for a light radiation mechanism 70 corresponding to the light source 60 having a luminous intensity distribution including repetitive high and low luminous intensity levels.

In a painting defect inspection by the light radiation mechanism 70 and a video camera 24, a robot controller 32 is driven by an instruction supplied from a host computer 31. The robot controller 32 supplies a drive control signal to a robot apparatus 21, and an internal actuator (not shown) of the robot apparatus 21 is operated. Thus, the robot apparatus 21 moves the light radiation mechanism 70 and the video camera 24 to trace the surface of a vehicle body. A received-light image obtained by the video camera 24 (corresponding to the received-light image shown in FIG. 19) is supplied to an image processor 33. The image processor 33 executes image processing by discriminating a level difference in brightness of the received-light image, and sends image-processed data to the host computer 31 to analyze it. The host computer 31 detects the presence/absence of a painting defect, and calculates the coordinates of the defect position.

Figure 22:
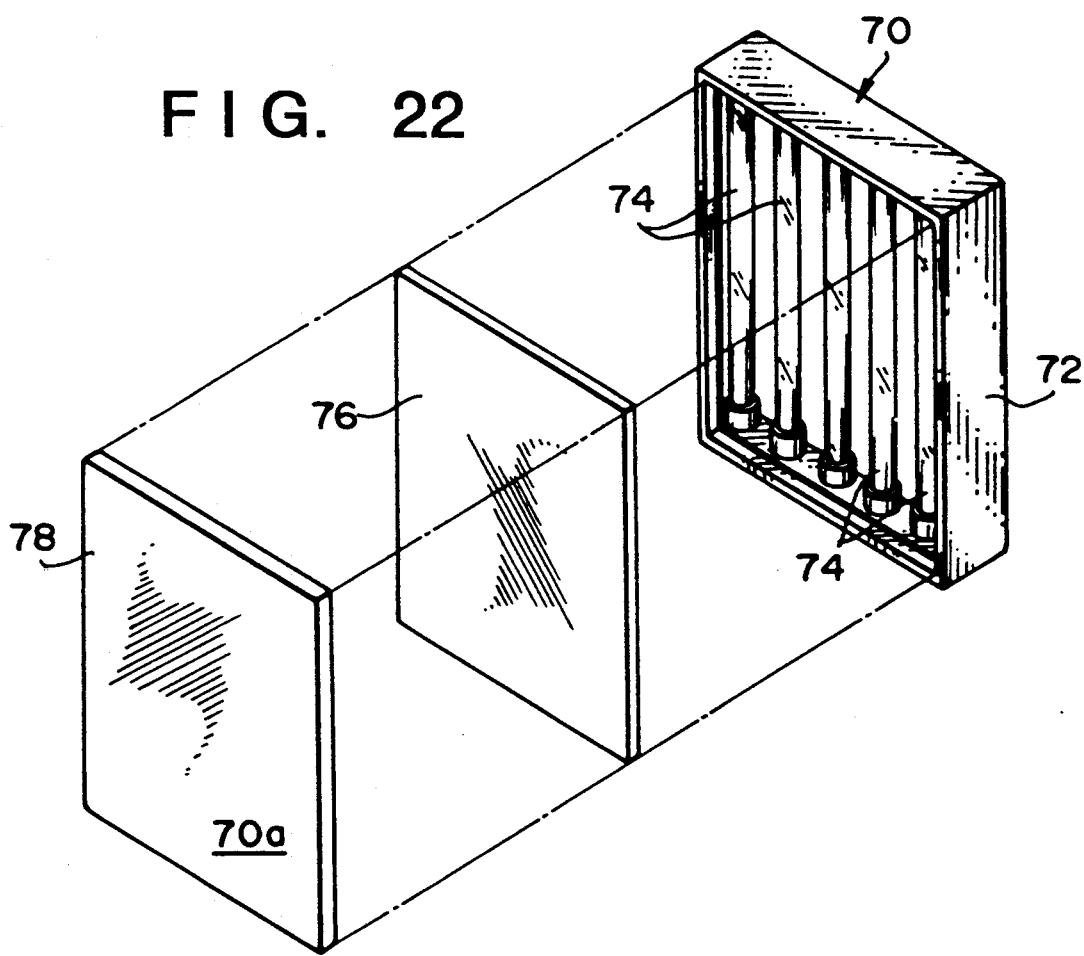
FIG. 22 is an exploded perspective view showing the structure of the light radiation mechanism shown in FIG. 20.

As shown in FIG. 22, the light radiation mechanism 70 is constituted by a box 72 with one open surface, a plurality of fluorescent lamps 74 (the present invention is not particularly limited to the fluorescent lamps) arranged in the box 72, a filter 76 arranged in front of these fluorescent lamps 74, and a diffusion screen 78 which is arranged to cover the front surface of the filter 76, and to cover the open surface of the box 72. The optical filter 76 is arranged to form high-level and low-level portions in a luminous intensity distribution of light emitted from the fluorescent lamps 74. More specifically, the optical filter 76 is formed to have different transmittance values depending on transmission positions. Thus, the surface of the diffusion screen 78 of the light radiation mechanism 70 serves as an output surface 70a having a change in luminous intensity described above. The diffusion screen 78 attains a smooth change in luminous intensity in a boundary between the regions having high and low luminous intensity levels formed on the output surface 70a. The diffusion screen 78 forms an ambiguous boundary of a change in luminous intensity of light transmitted therethrough to prevent a clear boundary of a change in luminous intensity from being formed.

Note that a change in luminous intensity of the light radiation mechanism 70 can be attained by changing application voltages to the fluorescent lamps 74. In this case, the optical filter 76 can be omitted.

In the painting defect inspection apparatus with the above arrangement, when a painted vehicle body 26 is conveyed into a painting inspection station 20, a painting defect inspection operation is started. When the painting defect inspection operation is started, the robot apparatus 21 moves the light radiation mechanism 70 and the video camera 24 to trace the surface pattern of the vehicle body while maintaining the predetermined positional relationship therebetween, and a proper distance between the surface of the vehicle body, and the light radiation mechanism 70 and the video camera 24, under the control of the robot controller 32. In this movement, the light radiation mechanism 70 radiates light having a luminous intensity distribution in which high and low intensity levels alternately appear over a relatively wide range covering at least a camera field F, as shown in FIG. 21. In FIG. 21, the length of each line segment represents a luminous intensity level. For this reason, an image of the light radiation mechanism 70 is reflected by the painted surface 27 serving as a mirror surface, and the video camera 24 forms a received-light image having bright and dark portions corresponding to the luminous intensity distribution of the light radiation mechanism 70.

Figure 19:
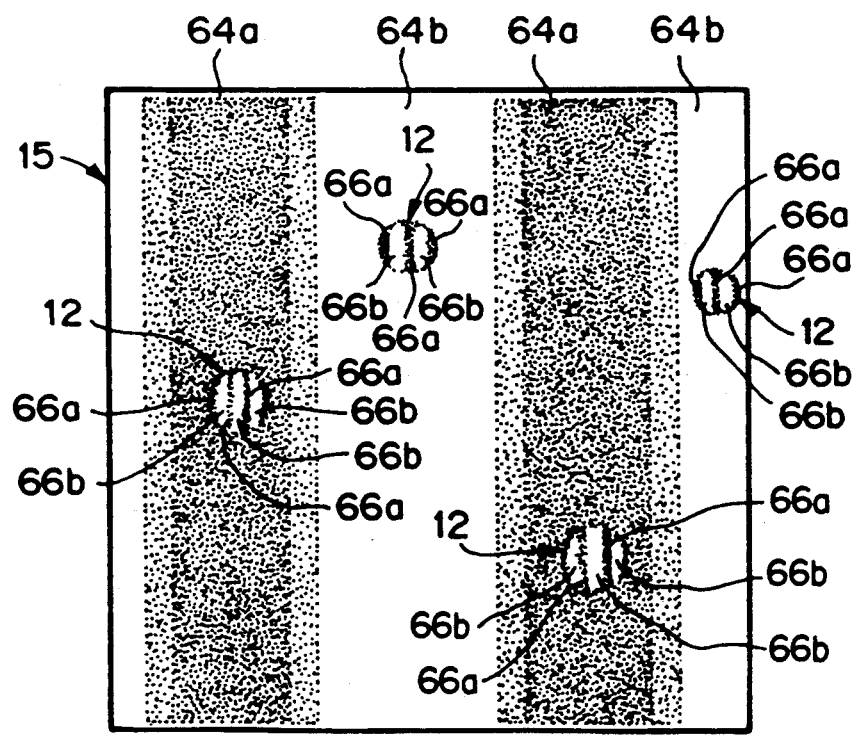
FIG. 19 is a view showing a formation state of an image obtained by a camera when a convex defect is present on a surface to be inspected.

Therefore, as has already been described in the description of the principle with reference to FIGS. 18 and 19, when a painting defect portion 28 is present on a region of the painted surface 27 of the vehicle body, which region reflects an image of the portion 62a having a low luminous intensity of the light radiation mechanism 70, regular reflection in a direction different from a normal portion occurs on the painting defect portion 28. As described above, the adjacent regions 66b and 66a respectively having high and low reflection luminous intensity levels are incident on the light-receiving surface of the camera. For this reason, as a received-light image, the painting defect portion 28 in which the bright and dark portions 66b and 66a are alternately present adjacent to each other is projected in the dark portion 64a, and the bright portion 66b is projected as a white dot.

When a painting defect portion 28 is formed on a region of the painted surface 27 of the vehicle body, which region reflects an image of the portion 62a having a low luminous intensity of the light radiation mechanism 70, regular reflection in a direction different from that of a normal portion similarly occurs on the painting defect portion 28. For this reason, as a received-light image, the painting defect portion 28 in which the adjacent bright and dark portions 66b and 66a are alternately present adjacent to each other is projected in the bright portion 64b, and the dark portion 66a is projected as a black dot.

For this reason, since a clear difference in brightness is formed between the white dot 66b and the dark portion 64a, or between the black dot 66a and the bright portion 64b, the host computer 31 can reliably check a level difference in brightness in image processing, and can precisely detect the painting defect portion 28.

Therefore, according to the third embodiment, even when light radiation is performed over a relatively wide range so as to execute an inspection on a curved surface portion of the vehicle body 26 without posing a problem, a painting defect inspection can be efficiently and precisely performed.

Figure 23:
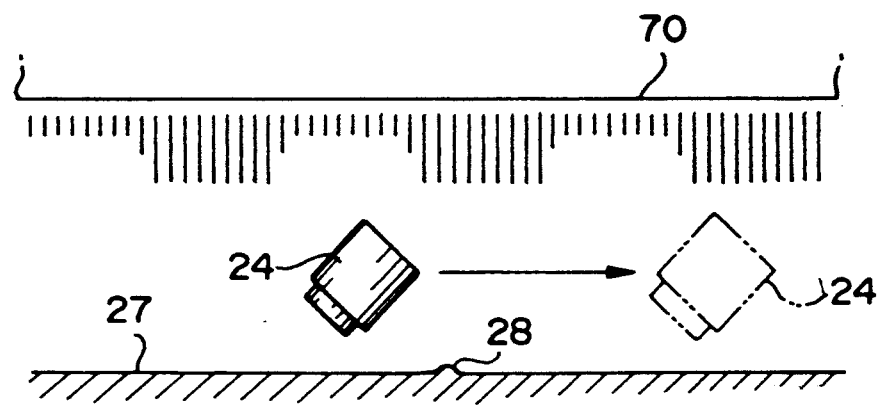
FIG. 23 is a schematic view showing a structure according to a modification of the third embodiment.

In the third embodiment described above, the light radiation mechanism 70 and the video camera 24 are moved to trace the surface of the vehicle body while maintaining the predetermined positional relationship therebetween. However, the third embodiment is not limited to this arrangement, but may be arranged as shown in FIG. 23 as the second modification of the third embodiment.

In the second modification, the light radiation mechanism 70, which has a wide light radiation region having a luminous intensity distribution in which high and low intensity levels alternately appear, radiates light on the entire inspection region of the painted surface 27. In the surface defect inspection of this modification, only the video camera 24 is moved along the painted surface 27. More specifically, in this modification, the painted surface 27 is traced by the video camera 24 to perform a defect inspection while the entire painted surface 27 is irradiated with light from the light radiation mechanism 70 having a luminous intensity distribution including high and low intensity levels. In this case, the painting defect portion 28 can be projected as an image having a clear level difference in brightness in a received-light image like in the third embodiment.

As can be apparent from the above description, in the third embodiment, the inspection surface serving as a mirror surface is irradiated with light having a luminous intensity distribution including high-level and low-level portions in place of light having a predetermined luminous intensity distribution, bright and dark portions can be formed in a received-light image of the camera for detecting reflected light from the light radiation mechanism, and bright and dark portions corresponding to the high-level and low-level portions of the luminous intensity distribution can also be formed in a reduced scale on a painting defect portion. As a result, when a painting defect portion is present on a portion of the painted surface, which portion reflects an image of a region having a low luminous intensity of regions for reflecting an image of the light radiation mechanism, the bright region formed on the painting defect portion is projected as a white dot in the dark portion in the received-light image. On the other hand, when a painting defect portion is present on a region having a high luminous intensity of regions for reflecting an image of the light radiation mechanism on the painted surface, a dark region formed on the painting defect portion is projected as a black dot in the bright portion in a received-light image.

Therefore, even when a defect inspection is performed while radiating light on a relatively wide region on the inspection surface, the painting defect portion can be clearly detected as a change in brightness in a received-light image. As a result, even a small defect portion can be reliably detected in image processing, and at the same time, a wide region and a curved surface region can be subjected to efficient defect inspection.

As many apparently widely different embodiments of the present invention can be made without departing from the spirit and scope thereof, it is to be understood that the invention is not limited to the specific embodiments thereof except as defined in the appended claims and equivalents thereof.

What is claimed is:

1. A surface defect inspection apparatus, which comprises:
   light radiation means, arranged to oppose a surface to be inspected serving as a mirror surface, for radiating light having a predetermined change pattern toward said surface to be inspected;
   imaging means for imaging an image of said light radiation means reflected by said surface to be inspected and forming a received-light image corresponding to the change pattern of said light radiation means;
   discriminating means for discriminating a surface defect portion at which a variation amount of said change pattern in the received-light image is different from that at a surrounding portion of the surface defect.

2. The apparatus according to claim 1, wherein said light radiation means radiates light having a luminous intensity distribution including high-level and low-level portions toward said surface to be inspected.

3. The apparatus according to claim 2, wherein
   said light radiation means radiates, toward said surface to be inspected, light having a luminous intensity distribution which is set so that a luminous intensity is gradually changed from high level to low level along a predetermined direction.

4. The apparatus according to claim 3, wherein
   said imaging means images the image of said light radiation means reflected by said surface to be inspected, and forms the received-light image corresponding to the luminous intensity distribution of said light radiation means.

5. The apparatus according to claim 4, wherein said discriminating means discriminates a portion whose change state of the luminous intensity distribution is different from a change state of a surrounding portion on the basis of the received-light image formed by said imaging means so as to detect the discriminated portion as the surface defect portion on said surface to be inspected.

6. The apparatus according to claim 1, wherein
said imaging means comprises a camera having a view field which is set to image the image of said light radiation means reflected by said surface to be inspected over an entire formation range of the received-light image.

7. The apparatus according to claim 6, wherein
said imaging means comprises video signal generation means for converting the received-light image into a video signal.

8. The apparatus according to claim 2, wherein
said light radiation means radiates light to have a luminous intensity distribution which is set such that high-level and low-level portions alternately appear.

9. The apparatus according to claim 8, wherein
said imaging means images the image of said light radiation means reflected by said surface to be inspected, and forms the received-light image having bright and dark portions corresponding to the luminous intensity distribution of said light radiation means.

10. The apparatus according to claim 9, wherein
said discriminating means discriminates a portion whose brightness is considerably different from a surrounding portion in each of the bright and dark portions on the basis of the received-light image formed by said imaging means so as to detect the discriminated portion as the surface defect portion of said surface to be inspected.

11. The apparatus according to claim 1, wherein
said light radiation means radiates, toward said surface to be inspected, light having a wavelength distribution which is set such that a wavelength is gradually changed from a long wavelength to a short wavelength in a predetermined direction.

12. The apparatus according to claim 11, wherein
said imaging means images the image of said light radiation means reflected by said surface to be inspected, and forms the received-light image having a wavelength distribution corresponding to the wavelength distribution of said light radiation means.

13. The apparatus according to claim 12, wherein said discriminating means discriminates a portion whose change state of the wavelength distribution is different from a change state of a surrounding portion on the basis of the received-light image formed by said imaging means so as to detect the discriminated portion as the surface defect portion on said surface to be inspected.

14. The apparatus according to claim 11, wherein
a wavelength of light radiated by said light radiation means is set in a visible light region.

15. The apparatus according to claim 1, wherein
said light radiation means radiates, toward said surface to be inspected, light having a color pattern in which colors are sequentially changed in a predetermined order along a predetermined direction.

16. The apparatus according to claim 15, wherein
said imaging means images the image of said light radiation means reflected by said surface to be inspected, and forms the received-light image having a color pattern corresponding to the color pattern of said light radiation means.

17. The apparatus according to claim 16, wherein said discriminating means discriminates a portion whose change state of the color pattern is different from a change state of a surrounding portion on the basis of the received-light image formed by said imaging means so as to detect the discriminated portion as the surface defect portion on said surface to be inspected.

18. A surface defect inspection apparatus comprising:
light radiation means, arranged to oppose a surface to be inspected serving as a mirror surface, for radiating light having a predetermined change pattern toward said surface to be inspected;
imaging means for imaging an image of said light radiation means reflected by said surface to be inspected and forming a received-light image corresponding to the change pattern of said light radiation means; and
image processing means for detecting a surface defect portion on said surface to be inspected by discriminating a portion whose change pattern is different from the change pattern on the basis of the received-light image formed by said imaging means,
wherein said light radiation means radiates light having a luminous intensity distribution including high-level and low-level portions toward said surface to be inspected,
wherein said light radiation means radiates, toward said surface to be inspected, light having the luminous intensity distribution which is set so that a luminous intensity is gradually changed from high level to low-level along a predetermined direction,
wherein said imaging means images the image of said light radiation means reflected by said surface to be inspected, and forms the received-light image corresponding to the luminous intensity distribution of said light radiation means, and
wherein when the change state of the luminous intensity distribution of the portion detected as the surface defect portion is the same as the change state of the luminous intensity distribution of the surrounding portion, said image processing means discriminates that the surface defect portion is formed in a convex shape, and when the change state of the luminous intensity distribution of the portion detected as the surface defect portion is opposite to the change state of the luminous intensity distribution of the surrounding portion, said image processing means discriminates that the surface defect portion is formed in a concave shape.

19. A surface defect inspection apparatus comprising:
light radiation means, arranged to oppose a surface to be inspected serving as a mirror surface, for radiating light having a predetermined change pattern toward said surface to be inspected;
imaging means for imaging an image of said light radiation means reflected by said surface to be inspected and forming a received-light image corresponding to the change pattern of said light radiation means; and
image processing means for detecting a surface defect portion on said surface to be inspected by discriminating a portion whose change pattern is different from the change pattern on the basis of the received-light image formed by said imaging means, wherein said imaging means comprises a camera having a view field which is set to image the image of said light radiating means reflected by said surface to be inspected over an entire formation range of the received-light image, wherein said imaging means comprises video signal generation means for converting the received-light image into a video signal, and wherein said image processing means processes the video signal output from said video signal generation means, and discriminates a position and a three-dimensional pattern of the surface defect portion on the basis of a timing at which the processed value exceeds a predetermined value, and a change state of the processed value.

20. A surface defect inspection apparatus comprising:

light radiation means, arranged to oppose a surface to be inspected serving as a mirror surface, for radiating light having a predetermined change pattern toward said surface to be inspected;

imaging means for imaging an image of said light radiation means reflected by said surface to be inspected and forming a received-light image corresponding to the change pattern of said light radiation means;

image processing means for detecting a surface defect portion on said surface to be inspected by discriminating a portion whose change pattern is different from the change pattern on the basis of the received-light image formed by said imaging means, wherein said light radiation means radiates, toward said surface to be inspected, light having a wavelength distribution which is set such that a wavelength is gradually changed from a long wavelength to a short wavelength in a predetermined direction, wherein said imaging means images the image of said light radiation means reflected by said surface to be inspected, and forms the received-light image having a wavelength distribution corresponding to the wavelength distribution of said light radiation means, wherein said image processing means discriminates a portion whose change state of the wavelength distribution is considerably different from a change state of a surrounding portion on the basis of the received-light image formed by said imaging means so as to detect the discriminated portion as the surface defect portion on said surface to be inspected, and wherein when the change state of the wavelength distribution of the portion detected as the surface defect portion is the same as the change state of the wavelength distribution of the surrounding portion, said image processing means discriminates that the surface defect portion is formed in a convex shape, and when the change state of the wavelength distribution of the portion detected as the surface defect portion is opposite to the change state of the wavelength distribution of the surrounding portion, said image processing means discriminates that the surface defect portion is formed in a concave shape.

21. A surface defect inspection apparatus comprising:

light radiation means, arranged to opposite a surface to be inspected serving as a mirror surface, for radiating light having a predetermined change pattern toward said surface to be inspected;

imaging means for imaging an image of said light radiation means reflected by said surface to be inspected and forming a received-light image corresponding to the change pattern of said light radiation means;

image processing means for detecting a surface defect portion on said surface to be inspected by discriminating a portion whose change pattern is different from the change pattern on the basis of the received-light image formed by said imaging means, wherein said light radiation means radiates, toward said surface to be inspected, light having a color pattern in which colors are sequentially changed in a predetermined order along a predetermined direction, wherein said imaging means images the image of said light radiation means reflected by said surface to be inspected, and forms the received-light image having a color pattern corresponding to the color pattern of said light radiation means, wherein said image processing means discriminates a portion whose change state of the color pattern is different from a change state of a surrounding portion on the basis of the received-light image formed by said imaging means so as to detect the discriminated portion as the surface defect portion on said surface to be inspected, and wherein when the change state of the color pattern of the portion detected as the surface defect portion is the same as the change state of the color pattern of the surrounding portion, said image processing means discriminates that the surface defect portion is formed in a convex shape, and when the change state of the color pattern of the portion detected as the surface defect portion is opposite to the change state of the color pattern of the surrounding portion, said image processing means discriminates that the surface defect portion is formed in a concave shape.

* * * * *